United States Patent
Yoshida et al.

(10) Patent No.: US 12,258,593 B2
(45) Date of Patent: Mar. 25, 2025

(54) HYDROLASE AND METHOD FOR PRODUCING (1S,2S)-1-ALKOXYCARBONYL-2-VINYL-CYCLOPROPANE CARBOXYLIC ACID USING SAME

(71) Applicant: UBE CORPORATION, Yamaguchi (JP)

(72) Inventors: Toyokazu Yoshida, Gifu (JP); Koichi Ishida, Gifu (JP); Ryoma Miyake, Tokyo (JP); Takanobu Iura, Tokyo (JP); Hiroshi Kawabata, Tokyo (JP)

(73) Assignee: UBE CORPORATION, Yamaguchi (JP)

( * ) Notice: Subject to any disclaimer, the term of this patent is extended or adjusted under 35 U.S.C. 154(b) by 0 days.

(21) Appl. No.: 18/091,687

(22) Filed: Dec. 30, 2022

(65) Prior Publication Data
US 2023/0323317 A1 Oct. 12, 2023

Related U.S. Application Data

(62) Division of application No. 17/043,339, filed as application No. PCT/JP2019/013926 on Mar. 29, 2019, now Pat. No. 11,572,551.

(30) Foreign Application Priority Data

Mar. 30, 2018 (JP) .................. 2018-070188

(51) Int. Cl.
*C12N 9/18* (2006.01)
*C12P 7/56* (2006.01)
*C12P 7/62* (2022.01)
*C12P 41/00* (2006.01)

(52) U.S. Cl.
CPC .............. *C12N 9/18* (2013.01); *C12P 7/62* (2013.01); *C12P 41/00* (2013.01); *C12Y 301/01* (2013.01)

(58) Field of Classification Search
CPC ..................................... C12N 9/18; C12P 7/62
See application file for complete search history.

(56) References Cited

U.S. PATENT DOCUMENTS

| | | | |
|---|---|---|---|
| 9,029,107 B2 * | 5/2015 | Kawabata | C12N 9/14 435/320.1 |
| 2013/0096339 A1 | 4/2013 | Asuma et al. | |
| 2013/0130338 A1 | 5/2013 | Kawabata et al. | |

FOREIGN PATENT DOCUMENTS

| | | |
|---|---|---|
| EP | 2 796 562 A1 | 10/2014 |
| JP | 5613660 B2 | 10/2014 |
| JP | 5657560 B2 | 1/2015 |
| WO | WO 2012/029819 A1 | 3/2012 |

OTHER PUBLICATIONS

Fransceus (J Ind Microbiol Biotechnol. May 2017;44(4-5):687-695.*

(Continued)

*Primary Examiner* — Yong D Pak
(74) *Attorney, Agent, or Firm* — Greenblum & Bernstein, P.L.C.

(57) ABSTRACT

The present invention provides a novel hydrolase that can industrially produce optically highly pure (1S,2S)-1-alkoxycarbonyl-2-vinylcyclopropane carboxylic acid with high efficiency at low costs, and a production method using the hydrolase.

7 Claims, 2 Drawing Sheets

Specification includes a Sequence Listing.

(56) References Cited

OTHER PUBLICATIONS

Sanavia (Computational and Structural Biotechnology Journal, vol. 18, 2020, pp. 1968-1979.*
F4CQZ7-PSEUX. UniProtKB/TrEMBL Database. Nov. 10, 2016.*
A0A0M8MNS3_9MICO. UniProtKB/TrEMBL Database. Sep. 27, 2027.*
ISR for PCT/JP2019/013926, dated Jun. 18, 2019, (w/ translation).
Written Opinion of the ISA for PCT/JP2019/013926, dated Jun. 18, 2019, (w/ translation).
EESR for EP App. No. 19777561.2, dated Jan. 10, 2022.
"Alpha/beta hydrolase {EC0:00003131 EMBL:OZC62876.1}", A0A259Y6X7, [online], UniProtKB, https://www.uniprot.org/uniprot/A0A259Y6X7.txt?version=3, Feb. 28, 2018.
"Alpha/beta hydrolase {EC0:00003131 EMBL:KQU47217.1}", A0A0Q6JV16, [online], UniProtKB, https://www.uniprot.org/uniprot/A0A0Q6JV16.txt?version=11, Feb. 28, 2018.
"Alpha/beta hydrolase [Pseudonocardia dioxanivorans]", WP_013673631, [online], National Center for Biotechnology Information, https://www.ncbi.nlm.nih.gov/protein/WP_013673631, May 18, 2013.
"Alpha/beta hydrolase [Microbacterium chocolatum]", WP_053548180, [online], National Center for Biotechnology Information, https://www.ncbi.nlm.nih.gov/protein/92489447?sat=47&satkey=7881781, Sep. 3, 2015.
Fliche et al., "Enantioselective Synthesis of (1R,2S) and (1S,2S) Dehydrocoronamic Acids," Synth. Commun. vol. 24, No. 20, pp. 2873-2876 (1994).
Database UniProt [Online], UniParc, Database accession No. UPI000B9AD34C, Dec. 20, 2017, XP002804883.
Database UniProt [Online], UniParc, Database accession No. UPI00070AAE76, Nov. 13, 2015, XP002804886.
Database UniProt [Online], UniParc, Database accession No. UPI00020740DB, Jun. 28, 2011, XP002804893.
Studer, "Residue mutations and their impact on protein structure and function: detecting beneficial and pathogenic changes," Biochem. J. (2013) 449, 581-594.
Office Action for CN App. No. 201980022337.3, dated Jan. 26, 2024 (w/ translation).

\* cited by examiner

Fig. 3

HYDROLASE AND METHOD FOR PRODUCING (1S,2S)-1-ALKOXYCARBONYL-2-VINYL-CYCLOPROPANE CARBOXYLIC ACID USING SAME

CROSS REFERENCE TO RELATED APPLICATIONS

This is a Divisional Application of U.S. application Ser. No. 17/043,339, which is the National Stage of International Application No. PCT/JP2019/013926, filed Mar. 29, 2019, which claims priority to Japanese Application No. 2018-070188, filed Mar. 30, 2018. The disclosures of each of the above-identified applications are expressly incorporated herein by reference in their entireties.

SEQUENCE LISTING

The content of the XML file of the sequence listing named "P67872_Sequence_Listing 06292023" that is 43,584 bytes in size and was created on Jun. 29, 2023, and was electronically submitted via Patent Center on Jun. 29, 2023, is herein incorporated by reference in its entirety.

TECHNICAL FIELD

The present invention relates to a novel hydrolase (esterase) that can be used for the production of (1S,2S)-1-alkoxycarbonyl-2-vinylcyclopropane carboxylic acid and use thereof.

BACKGROUND ART (1S,2S)-1-alkoxycarbonyl-2-vinylcyclopropane carboxylic acid is an intermediate useful for the production of various HCV NS3 protease inhibitors under development as a therapeutic drug for hepatitis C and the like.

Non-patent document 1, patent document 1 and patent document 2 describe a method for obtaining (1S,2S)-1-methoxycarbonyl-2-vinylcyclopropane carboxylic acid by hydrolyzing dimethyl 2-vinylcyclopropane-1,1-dicarboxylic acid by an enzyme.

However, the enzyme used in non-patent document 1 has insufficient optical selectivity, and the obtained (1S,2S)-1-methoxycarbonyl-2-vinylcyclopropane carboxylic acid has insufficient optical purity of 90% e.e., and thus the enzyme is not suitable for an industrial production method of an intermediate for a pharmaceutical product. The enzymes used in patent document 1 and patent document 2 have insufficient optical selectivity, a by-product (1S,2R)-1-methoxycarbonyl-2-vinylcyclopropane carboxylic acid is produced in a large amount besides the desired (1S,2S)-1-methoxycarbonyl-2-vinylcyclopropane carboxylic acid, which renders highly efficient production of the target product difficult to achieve. For industrial production, large separation device and large purification device are required, which increases the cost.

Therefore, a method for industrially producing (1S,2S)-1-alkoxycarbonyl-2-vinylcyclopropane carboxylic acid with high purity and high efficiency at low costs which is useful as an intermediate for the production of a therapeutic drug for hepatitis C and the like has been desired.

DOCUMENT LIST

Patent Documents patent document 1: JP-B-5613660
patent document 2: JP-B-5657560

Non-Patent Document non-patent document 1: C. Fliche et al. Synth. Commun. 24(20), 2873-2876 (1994)

SUMMARY OF INVENTION

Technical Problem

The problem to be solved by the present invention is provision of a novel hydrolase (esterase) for producing (1S,2S)-1-alkoxycarbonyl-2-vinylcyclopropane carboxylic acid with high optical purity and high selectivity. Furthermore, the problem to be solved by the present invention is provision of a novel method for industrially producing optically highly pure (1S,2S)-1-alkoxycarbonyl-2-vinylcyclopropane carboxylic acid with high efficiency at low costs.

Solution to Problem

The present inventors have conducted intensive studies in an attempt to solve the aforementioned problems and found that enzymes derived from *Rhodococcus* sp. D32 strain, *Pseudonocardia dioxanivorans* CB1190 strain, and *Microbacterium chocolatum* hydrolyze dialkyl 2-vinylcyclopropane-1,1-dicarboxylic acid with high selectivity and can afford (1S,2S)-1-alkoxycarbonyl-2-vinylcyclopropane carboxylic acid with high efficiency. They have also found that (1S,2S)-1-alkoxycarbonyl-2-vinylcyclopropane carboxylic acid with high optical purity, high selectivity and high concentration can be obtained at low costs by bringing the enzyme, a microorganism or cell having an ability to produce the enzyme, a treated product of the microorganism or cell, and/or a culture solution containing the enzyme obtained by culturing the microorganism or cell (hereinafter these are sometimes collectively referred to as "enzyme, etc.") into contact with dialkyl 2-vinylcyclopropane-1,1-dicarboxylic acid. Furthermore, they have found that optically highly pure (1R,2S)-1-amino-1-alkoxycarbonyl-2-vinylcyclopropane can also be produced with high efficiency at low costs by using the thus-obtained (1S,2S)-1-alkoxycarbonyl-2-vinylcyclopropane carboxylic acid. The present invention was completed based on these findings.

That is, the present invention provides the following.

[1] A hydrolase comprising a polypeptide of any of the following (a)-(e):
(a) a polypeptide having the amino acid sequence shown in SEQ ID NO: 2
(b) a polypeptide having the amino acid sequence shown in SEQ ID NO: 4 or 6, and an activity to catalyze the reaction shown in the formula (1):

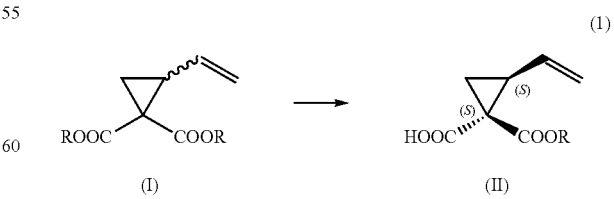

wherein R is an alkyl group having 1-6 carbon atoms
(c) a polypeptide having an amino acid sequence resulting from the deletion, insertion, substitution and/or addition of one or plural amino acids in the amino acid sequence shown in SEQ ID NO: 2, 4 or 6, and an activity to catalyze the reaction shown in the formula (1)

(d) a polypeptide having an amino acid sequence with not less than 60% of sequence identity with the amino acid sequence shown in SEQ ID NO: 2, 4 or 6, and an activity to catalyze the reaction shown in the above-mentioned formula (1)

(e) a polypeptide having an amino acid sequence with not less than 60% of sequence identity with the amino acid sequence shown in SEQ ID NO: 2, 4 or 6, wherein the aforementioned amino acid sequence comprises one or more motif sequences selected from the following motif sequences (i)-(iv)

(i) a sequence consisting of 5 consecutive residues (aspartic acid (D), alanine (A), threonine (T), arginine (R), glycine (G))

(ii) a sequence consisting of 4 consecutive residues (proline (P), tyrosine (Y), glycine (G), phenylalanine (F))

(iii) a sequence consisting of 4 consecutive residues (asparagine (N), tryptophan (W), proline (P), glycine (G))

(iv) a sequence consisting of 5 consecutive residues (proline (P), glycine (G), tryptophan (W), proline (P), glycine (G)).

[2] The hydrolase of [1], wherein R in the formula (1) is an ethyl group.

[3] A nucleic acid encoding hydrolase of [1] or [2].

[4] The nucleic acid of [3], wherein the aforementioned nucleic acid comprises a base sequence of the following (f), (g), (h) or (i):

(f) the base sequence shown in SEQ ID NO: 1, 3 or 5

(g) a nucleic acid having a base sequence resulting from the substitution, deletion, and/or addition of one or plural bases in the base sequence shown in SEQ ID NO: 1, 3 or 5, and encoding a polypeptide having an activity to catalyze the reaction shown in the formula (1)

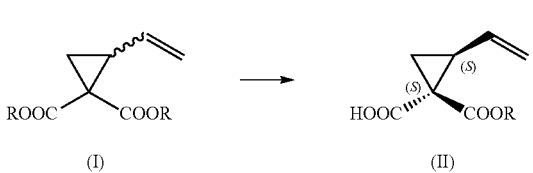

wherein R is an alkyl group having 1-6 carbon atoms (h) a nucleic acid having a base sequence having not less than 60% of sequence identity with the base sequence shown in SEQ ID NO: 1, 3 or 5, and encoding a polypeptide having an activity to catalyze the reaction shown in the above-mentioned formula (1) (i) a nucleic acid having a base sequence that hybridizes with a complementary strand of the base sequence shown in SEQ ID NO: 1, 3 or 5 under stringent conditions, and encoding a polypeptide having an activity to catalyze the reaction shown in the above-mentioned formula (1).

[5] A method for producing (1S,2S)-1-alkoxycarbonyl-2-vinylcyclopropane carboxylic acid, comprising bringing the hydrolase of [1] or [2], a microorganism or cell having an ability to produce the aforementioned enzyme, a treated product of the aforementioned microorganism or cell, and/or a culture solution containing the aforementioned enzyme obtained by culturing the aforementioned microorganism or cell into contact with dialkyl 2-vinylcyclopropane-1,1-dicarboxylic acid represented by the formula (I) to produce (1S,2S)-1-alkoxycarbonyl-2-vinylcyclopropane carboxylic acid represented by the formula (II).

[6] The production method of [5], wherein the aforementioned microorganism or cell is a microorganism or cell transformed with the nucleic acid of [3] or [4].

[7] The recombinant vector comprising the nucleic acid of [3] or [4].

[8] A transformant comprising the recombinant vector of [7].

Advantageous Effects of Invention

According to the present invention, a novel hydrolase (esterase) for producing (1S,2S)-1-alkoxycarbonyl-2-vinylcyclopropane carboxylic acid which is useful as an intermediate for the production of a therapeutic drug for hepatitis C and the like can be provided with high optical purity and high selectivity. In addition, according to the present invention, a novel method for industrially producing optically highly pure (1S,2S)-1-alkoxycarbonyl-2-vinylcyclopropane carboxylic acid with high efficiency at low costs can be provided. Furthermore, optically highly pure (1R,2S)-1-amino-1-alkoxycarbonyl-2-vinylcyclopropane can be produced with high efficiency at low costs by using the thus-obtained (1S,2S)-1-alkoxycarbonyl-2-vinylcyclopropane carboxylic acid.

The (1S,2S)-1-alkoxycarbonyl-2-vinylcyclopropane carboxylic acid produced by the method of the present invention, and (1R,2S)-1-amino-1-alkoxycarbonyl-2-vinylcyclopropane produced using same can be utilized as a starting material or an intermediate for production in the production of a therapeutic drug for hepatitis C and the like.

BRIEF DESCRIPTION OF DRAWINGS

FIG. 3 shows the alignment of hydrolases.

DESCRIPTION OF EMBODIMENTS

Figure 1:
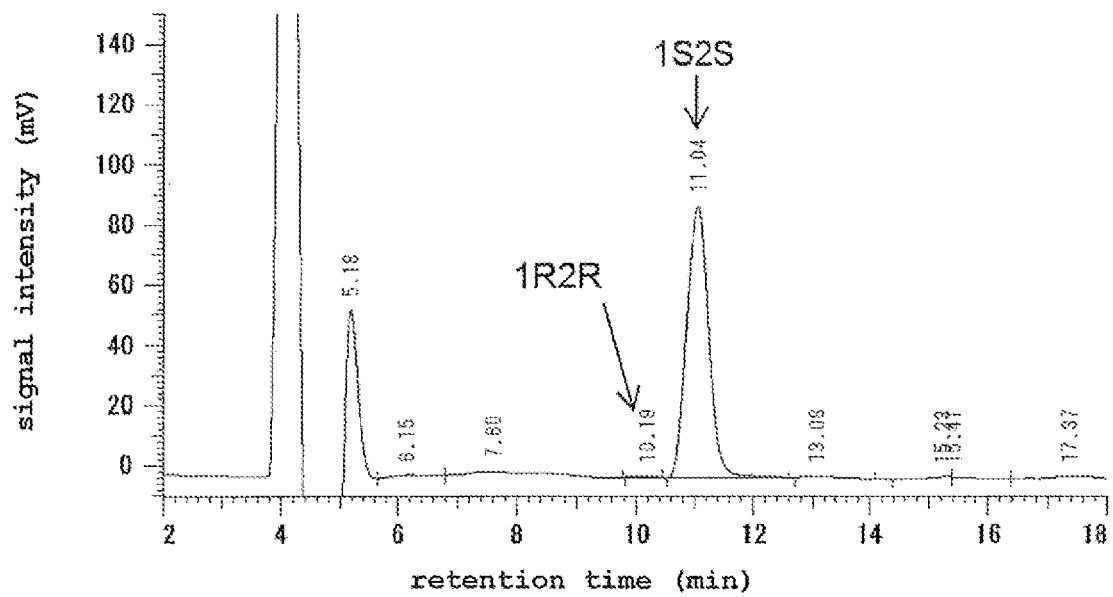
FIG. 1 shows HPLC analysis results of the reaction product obtained using a bacterium having the amino acid sequence D32Est in Example 1.

The present invention is explained in detail below.

1. Hydrolase of the Present Invention

The hydrolase of the present invention is one containing a polypeptide having the amino acid sequence shown in SEQ ID NO: 2, 4 or 6, or one containing a polypeptide having an amino acid sequence having high identity with the amino acid sequence (hereinafter sometimes to be referred to as "the homologue of the amino acid sequence") and having an activity to hydrolyze diethyl 2-vinylcyclopropane-1,1-dicarboxylic acid (hereinafter sometimes to be referred to as "the homologue of hydrolase"). Specifically, the novel hydrolase of the present invention contains a polypeptide of the following (a), (b), (c), (d) or (e):

(a) a polypeptide having the amino acid sequence shown in SEQ ID NO: 2

(b) a polypeptide having the amino acid sequence shown in SEQ ID NO: 4 or 6, and an activity to catalyze the reaction shown in the formula (1):

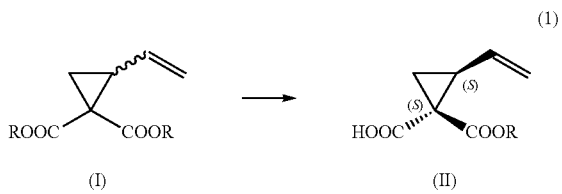

wherein R is an alkyl group having 1-6 carbon atoms
(c) a polypeptide having an amino acid sequence resulting from the deletion, insertion, substitution and/or addition of one or plural amino acids in the amino acid sequence shown in SEQ ID NO: 2, 4 or 6, and an activity to catalyze the reaction shown in the formula (1)
(d) a polypeptide having an amino acid sequence with not less than 60% of sequence identity with the amino acid sequence shown in SEQ ID NO: 2, 4 or 6, and an activity to catalyze the reaction shown in the above-mentioned formula (1)
(e) a polypeptide having an amino acid sequence with not less than 60% of sequence identity with the amino acid sequence shown in SEQ ID NO: 2, 4 or 6, wherein the aforementioned amino acid sequence comprises one or more motif sequences selected from the following motif sequences (i)-(iv)
(i) a sequence consisting of 5 consecutive residues (aspartic acid (D), alanine (A), threonine (T), arginine (R), glycine (G))
(ii) a sequence consisting of 4 consecutive residues (proline (P), tyrosine (Y), glycine (G), phenylalanine (F))
(iii) a sequence consisting of 4 consecutive residues (asparagine (N), tryptophan (W), proline (P), glycine (G))
(iv) a sequence consisting of 5 consecutive residues (proline (P), glycine (G), tryptophan (W), proline (P), glycine (G)).

In the formula (1), the alkyl group having 1-6 carbon atoms for R is, for example, a linear or branched alkyl group having 1-6 carbon atoms, more preferably a linear or branched alkyl group having 1-3 carbon atoms. Specific examples include methyl group, ethyl group, isopropyl group, normal propyl group, normal butyl group, isobutyl group, sec-butyl group, tert-butyl group, normal pentyl group, isopentyl group, tert-pentyl group, neopentyl group, normal hexyl group and the like. Among these, methyl group and ethyl group are preferable, and ethyl group is particularly preferable. In the formula (I), two Rs may be the same or different, preferably the same.

In the present invention, the homologue of a hydrolase with the amino acid sequence shown in SEQ ID NO: 2, 4 or 6 contains the polypeptide shown in the aforementioned (c), (d) or (e).

The polypeptide of the aforementioned (c) is a polypeptide having an amino acid sequence resulting from the deletion, insertion, substitution and/or addition of one or plural amino acids in the amino acid sequence shown in SEQ ID NO: 2, 4 or 6, and an activity to catalyze the reaction shown in the formula (1). In the case of substitution, one in which one or plural amino acids are conservatively substituted is preferable. In the present specification, that the "amino acids are conservatively substituted" means substitution of amino acids having similar chemical properties and the like and, for example, substitution of a basic amino acid with a basic amino acid and substitution of an acidic amino acid with an acidic amino acid can be mentioned.

The "one or plural amino acids" means generally 1-100, preferably 1-50, more preferably 1-20, further preferably 1-10, particularly preferably 1-5, amino acids.

The polypeptide of the aforementioned (d) is a polypeptide having an amino acid sequence with not less than 60% of sequence identity with the amino acid sequence shown in SEQ ID NO: 2, 4 or 6, and an activity to catalyze the reaction shown in the above-mentioned formula (1). Preferably, it is a polypeptide having an amino acid sequence with not less than 80%, more preferably not less than 90%, further preferably not less than 95%, of sequence identity with the full-length amino acid sequence shown in SEQ ID NO: 2, 4 or 6, and an activity to catalyze the reaction shown in the above-mentioned formula (1).

The homology (to be also referred to as identity or similarity) of the amino acid sequences in the present specification can be calculated using homology calculation algorithm NCBI BLAST (National Center for Biotechnology Information Basic Local Alignment Search Tool) and, for example, under the following conditions (expectancy=10; gap allowed; matrix=BLOSUM62; filtering=OFF). Examples of other algorithm for determining the homology of the amino acid sequence include the algorithm described in Karlin et al., Proc. Natl. Acad. Sci. USA, 90: 5873-5877 (1993) [said algorithm is incorporated in the NBLAST and XBLAST program (version 2.0) (Altschul et al., Nucleic Acids Res., 25: 3389-3402 (1997))], the algorithm described in Needleman et al., J. Mol. Biol., 48: 444-453 (1970) [said algorithm is incorporated in the GAP program in the GCG software package], the algorithm described in Myers and Miller, CABIOS, 4: 11-17 (1988) [said algorithm is incorporated in ALIGN program (version2.0) which is a part of the CGC sequence alignment software package], the algorithm described in Pearson et al., Proc. Natl. Acad. Sci. USA, 85: 2444-2448 (1988) [said algorithm is incorporated in the FASTA program in the GCG software package] and the like, and these can also be similarly used preferably.

In the present invention, the activity to catalyze the reaction shown in the formula (1) is an activity to catalyze the reaction of hydrolyzing dialkyl 2-vinylcyclopropane-1,1-dicarboxylic acid represented by the formula (I) to produce (1S,2S)-1-alkoxycarbonyl-2-vinylcyclopropane carboxylic acid represented by the formula (II).

There are two kinds of stereoisomers ((2R) isomer and (2S) isomer) of dialkyl 2-vinylcyclopropane-1,1-dicarboxylic acid. Unless there are special conditions that cause inversion of configuration at the 2-position, (2S) isomer alone can be basically the starting material of the (1S,2S)-1-alkoxycarbonyl-2-vinylcyclopropane carboxylic acid of interest.

Therefore, the activity to catalyze the reaction shown in the formula (1) is an activity to catalyze the reaction with selectivity of preferentially hydrolyzing only the pro-R alkoxycarbonyl group from the two alkoxycarbonyl groups bonded to the prochiral carbon at the 1-position of dialkyl (2S)-2-vinylcyclopropane-1,1-dicarboxylic acid to preferentially produce (1S,2S)-1-alkoxycarbonyl-2-vinylcyclopropane carboxylic acid.

The pro-R is a notation that distinguishes between two Xs on $CX_2YZ$, and determines the priority order of respective substituents on C according to the CIP rule. Assuming that one of the two Xs has a higher priority order than the other, the relationship of the priority order with Y and Z is not changed. Based on the tentative priority order, whether the chirality of the central carbon is R or S is determined by the RS notation. In the case of R isomer, the priority X at that time is set as pro-R, and in the case of S isomer, it is set as pro-S.

This selectivity can be confirmed using the ratio of (1S,2S) isomer and (1R,2S) isomer of 1-alkoxycarbonyl-2-vinylcyclopropane carboxylic acid produced by hydrolysis as an index. The lower the amount of (1R,2S) isomer produced is compared to the amount of (1S,2S) isomer produced, the more improved is the yield of (1S,2S)-1-alkoxycarbonyl-2-vinylcyclopropane carboxylic acid, which is advantageous for industrialization.

The production ratio of the (1S,2S) isomer and the (1R,2S) isomer can be compared using the ratio of the Anti isomer produced and the Syn isomer produced as an index. The Anti isomer and Syn isomer refer to geometric isomers, the (1S,2S) isomer and the (1R,2R) isomer are Anti isomers, and the (1R,2S) isomer and the (1S,2R) isomer are Syn isomers. In the present invention, since the product resulting from hydrolysis is mainly composed of the (1S,2S) isomer, the resultant product can be quantified not only by the evaluation system for quantifying the (1S,2S) isomer alone, but also an evaluation system capable of separating an Anti isomer and a Syn isomer. That is, when the (1S,2S) isomer is quantified, it can be replaced by quantification of the amount of Anti isomer produced. Similarly, when the (1R,2S) isomer is quantified, it can be replaced by quantification of the amount of Syn isomer produced. The lower the ratio of Syn isomer produced is, the more improved is the yield of (1S,2S)-1-alkoxycarbonyl-2-vinylcyclopropane carboxylic acid, which is advantageous for industrialization.

These selectivities can be confirmed by contacting a racemate dialkyl 2-vinylcyclopropane-1,1-dicarboxylic acid with the hydrolase of interest and the like to produce 1-alkoxycarbonyl-2-vinylcyclopropane carboxylic acid, and measuring the amount of the (1S,2S) isomer and the (1R,2S) isomer of 1-alkoxycarbonyl-2-vinylcyclopropane carboxylic acid produced, or by measuring the amount of the Anti isomer and the Syn isomer produced.

The contact method is not particularly limited and includes, for example, adding racemic dialkyl 2-vinylcyclopropane-1,1-dicarboxylic acid to a liquid containing the aforementioned hydrolase of interest, and reacting them at a suitable temperature (e.g., about 10° C.-45° C.) and pressure (e.g., about atmospheric pressure) and the like.

When the racemic dialkyl 2-vinylcyclopropane-1,1-dicarboxylic acid is hydrolyzed, hydrolysis of (2R) isomer results in the production of (1S,2R) isomer and (1R,2R) isomer. It is preferable to suppress the production amount of (1R,2R) isomer to a low level, which is the enantiomer of the (1S,2S) isomer of interest. Therefore, in the present invention, it is more preferable to have selectivity to preferentially produce (1S,2R)-1-alkoxycarbonyl-2-vinylcyclopropane carboxylic acid by preferentially hydrolyzing only a pro-R alkoxycarbonyl group from the two alkoxycarbonyl groups bonded to the prochiral carbon at the 1-position of dialkyl (2R)-2-vinylcyclopropane-1,1-dicarboxylic acid. Similarly, it is further preferable to have selectivity to preferentially hydrolyze dialkyl (2S)-2-vinylcyclopropane-1,1-dicarboxylic acid than dialkyl (2R)-2-vinylcyclopropane-1,1-dicarboxylic acid. The both selectivities can be measured by enantiomeric excess (% e.e.) of (1S,2S) isomer with respect to the (1R,2R) isomer of 1-alkoxycarbonyl-2-vinylcyclopropanecarboxylic acid produced by hydrolysis. The higher the enantiomeric excess of the (1S,2S) isomer, the less likely it is that the subsequent production process and the physiological activity of the produced pharmaceutical product will be adversely affected, which is industrially advantageous.

The polypeptide of the aforementioned (e) is a polypeptide having an amino acid sequence with not less than 60% of sequence identity with the amino acid sequence shown in SEQ ID NO: 2, 4 or 6, wherein the amino acid sequence comprises one or more motif sequences selected from the following motif sequences (i)-(iv)
  (i) a sequence consisting of 5 consecutive residues (aspartic acid (D), alanine (A), threonine (T), arginine (R), glycine (G))
  (ii) a sequence consisting of 4 consecutive residues (proline (P), tyrosine (Y), glycine (G), phenylalanine (F))
  (iii) a sequence consisting of 4 consecutive residues (asparagine (N), tryptophan (W), proline (P), glycine (G))
  (iv) a sequence consisting of 5 consecutive residues (proline (P), glycine (G), tryptophan (W), proline (P), glycine (G)).

Figure 3:
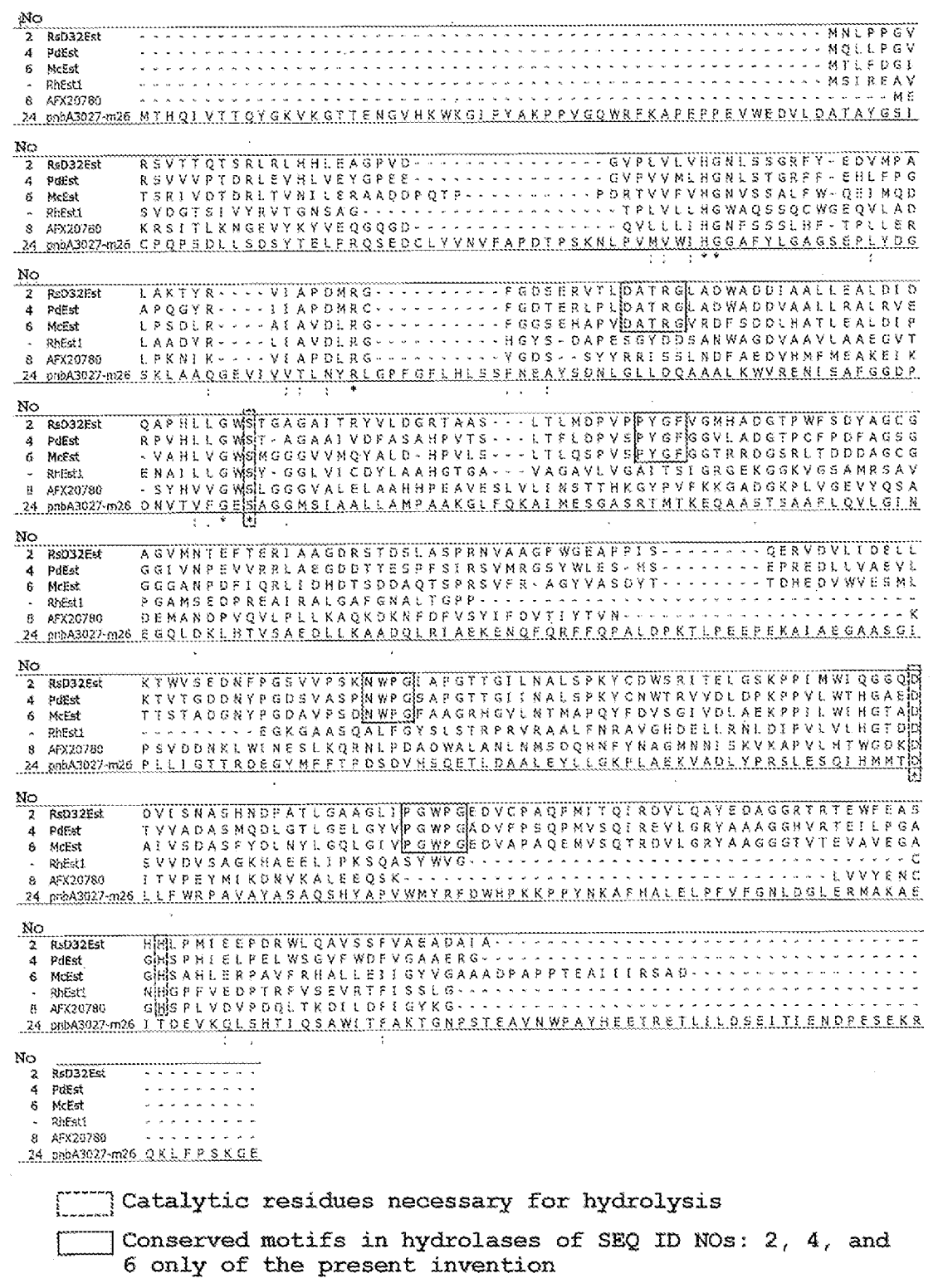

In the present invention, the motif sequence refers to a small structural portion found in the amino acid sequence of a polypeptide. It is known that a group of polypeptides (proteins) that retain a particular function have a common characteristic motif sequence. For example, it is known that serine (S), aspartic acid (D), and histidine (H) are amino acid residues necessary for catalytic activity (hydrolyzing function) in a particular kind of hydrolase. Specifically, the hydrolase RhEst1 shown in Catalysis Science and Technology, 2015, vol. 5, 2622 has serine (S), aspartic acid (D) and histidine (H) as amino acid residues. As shown in FIG. 3, the hydrolase AFX20780 described in U.S. Pat. No. 8,298,799 also has serine (S), aspartic acid (D) and histidine (H) as amino acid residues at particular positions.

As shown in FIG. 3, the amino acid sequence shown in SEQ ID NO: 2, 4 or 6 of the present invention also has serine (S), aspartic acid (D) and histidine (H) at particular positions, similar to the aforementioned hydrolase RhEst1 and AFX20780, and has catalytic activity (hydrolysis function).

As shown in FIG. 3, the amino acid sequence shown in SEQ ID NO: 2, 4 or 6 of the present invention has, as characteristic motif sequence (s), one or more motif sequences selected from the following motif sequences (i)-(iv)
  (i) a sequence consisting of 5 consecutive residues (aspartic acid (D), alanine (A), threonine (T), arginine (R), glycine (G))
  (ii) a sequence consisting of 4 consecutive residues (proline (P), tyrosine (Y), glycine (G), phenylalanine (F))
  (iii) a sequence consisting of 4 consecutive residues (asparagine (N), tryptophan (W), proline (P), glycine (G))
  (iv) a sequence consisting of 5 consecutive residues (proline (P), glycine (G), tryptophan (W), proline (P), glycine (G)).

These motif sequences are commonly possessed by the amino acid sequences shown in SEQ ID NO: 2, 4 and 6 of the present invention besides the aforementioned serine (S), aspartic acid (D) and histidine (H). It is thus presumed that they are motif sequences for stereoselectively hydrolyzing dialkyl 2-vinylcyclopropane-1,1-dicarboxylic acid, which is the characteristic function of the enzyme of the present invention having the amino acid sequence. These motif sequences may function independently, or a plurality of motif sequences may act simultaneously to exert the desired function.

As described above, the hydrolase of the present invention contains a polypeptide having the amino acid sequence shown in SEQ ID NO: 2, 4 or 6, or is a homologue of the amino acid sequence and containing a polypeptide having a hydrolytic activity on dialkyl 2-vinylcyclopropane-1,1-dicarboxylic acid. The level of the activity of the hydrolase containing a polypeptide having the homologue of the amino acid sequence to hydrolyze dialkyl 2-vinylcyclopropane-1,1-dicarboxylic acid may be quantitatively equivalent to that of a hydrolase containing a polypeptide having the amino acid sequence shown in SEQ ID NO: 2, 4 or 6, or may vary within an acceptable range (e.g., about 0.1—about 5 times, preferably about 0.3—about 3 times).

The amino acid sequences shown in SEQ ID NO: 2, 4 and 6 are each derived from *Rhodococcus* sp. D32 strain, *Pseudonocardia dioxanivorans* CB1190 strain and *Microbacterium chocolatum*. These amino acid sequences were identified by the present inventors to be hydrolases of dialkyl 2-vinylcyclopropane-1,1-dicarboxylic acid.

The polypeptide having the amino acid sequence shown in SEQ ID NO: 2 is a polypeptide derived from *Rhodococcus* sp. D32 strain, and the strain is a bacterium recovered from a soil sample. The amino acid sequence shown in SEQ ID NO: 2 was obtained by the analysis of the N-terminal sequence of dialkyl 2-vinylcyclopropane-1,1-dicarboxylic acid hydrolase produced by the bacterium and the analysis of the chromosomal DNA of *Rhodococcus* sp. D32 strain.

The polypeptides having the amino acid sequences shown in SEQ ID NO: 4 and 6 are sequences obtained from the genomic information of the microorganisms from which they are derived. The amino acid sequences shown in SEQ ID NO: 4 and 6 are respectively the same as GenBank accession Nos. WP-013673631 and WP-053548180 which are amino acid sequences encoded by a DNA sequence predicted to encode a protein. There are no reports that actually confirmed the existence of any of them, such as isolation as a protein. Naturally, their function as a protein was completely unknown.

In the present invention, a polypeptide having the amino acid sequence shown in SEQ ID NO: 2 is preferable since it shows high yield of (1S,2S)-1-alkoxycarbonyl-2-vinylcyclopropane carboxylic acid and high selectivity among the polypeptides having the amino acid sequences shown in SEQ ID NO: 2, 4 and 6.

The hydrolase containing a polypeptide having the amino acid sequence shown in SEQ ID NO: 2, 4 or 6 of the present invention can also be obtained from *Rhodococcus* sp. D32 strain, *Pseudonocardia dioxanivorans* CB1190 strain, or *Microbacterium chocolatum*, respectively, by purification and isolation by a known method. Examples of the purification method include solvent extraction, distillation, column chromatography, liquid chromatography, recrystallization, combination thereof and the like.

In addition, the hydrolase of the present invention can also be produced by culturing a transformant containing a nucleic acid encoding same, and separating and purifying the hydrolase from the obtained culture. The nucleic acid encoding the hydrolase of the present invention may be a DNA or an RNA, or DNA/RNA chimera. It is preferably a DNA. The nucleic acid may be double stranded or single stranded. When the nucleic acid is double stranded, it may be a double stranded DNA, a double stranded RNA or a DNA:RNA hybrid. When the nucleic acid is single stranded, it may be a sense strand (that is, coding strand) or antisense strand (that is, non-coding strand).

As the DNA encoding the hydrolase of the present invention, synthetic DNA or the like can be mentioned. For example, it can be obtained by converting full-length hydrolase cDNA which was directly amplified by Reverse Transcriptase-PCR using total RNA or mRNA fraction prepared from the cells or tissues derived from *Rhodococcus* sp. D32 strain, *Pseudonocardia dioxanivorans* CB1190 strain or *Microbacterium chocolatum* as a template, according to a method known per se such as ODA-LA PCR method, Gapped duplex method, Kunkel method and the like or a method analogous thereto, and using a known kit, for example, MutanTM-super Express Km (TAKARA BIO INC.), MutanTM-K (TAKARA BIO INC.) or the like. Alternatively, it can also be obtained from a cDNA library prepared by inserting the above-mentioned total RNA or mRNA fragments in suitable vectors, by converting, according to the above-mentioned method, the cDNA cloned by a colony or plaque hybridization method, PCR method or the like. The vector used for the library may be any such as bacteriophage, plasmid, cosmid, phagemid or the like.

Examples of the nucleic acid encoding the polypeptide having the amino acid sequence shown in SEQ ID NO: 2, 4 or 6 include nucleic acids containing the base sequence shown in SEQ ID NO: 1, 3 or 5, respectively. It may be a nucleic acid containing a base sequence having high identity with the base sequence of SEQ ID NO: 1, 3 or 5 (hereinafter sometimes to be referred to as "nucleic acid homologue") as long as it encodes a polypeptide having the activity to catalyze the reaction shown by the formula (1). That is, examples of the nucleic acid encoding the polypeptide include those having the base sequence shown in the following (f), (g), (h) or (i):

(f) a nucleic acid having the base sequence shown in SEQ ID NO: 1, 3 or 5

(g) a nucleic acid having a base sequence resulting from the substitution, deletion, and/or addition of one or plural bases in the base sequence shown in SEQ ID NO: 1, 3 or 5, and encoding a polypeptide having an activity to catalyze the reaction shown in the above-mentioned formula (1)

(h) a nucleic acid having a base sequence having not less than 60% of sequence identity with the base sequence shown in SEQ ID NO: 1, 3 or 5, and encoding a polypeptide having an activity to catalyze the reaction shown in the above-mentioned formula (1)

(i) a nucleic acid having a base sequence that hybridizes with a complementary strand of the base sequence shown in SEQ ID NO: 1, 3 or 5 under stringent conditions, and encoding a polypeptide having an activity to catalyze the reaction shown in the above-mentioned formula (1).

The homologue of the nucleic acid of the aforementioned (g) is, for example, a nucleic acid containing a base sequence resulting from deletion, substitution, insertion and/or addition of one or plural bases in the base sequence shown in SEQ ID NO: 1, 3 or 5 and encoding a polypeptide having an activity to catalyze the reaction shown in the above-mentioned formula (1). In the case of substitution, insertion or addition, one or plural bases are preferably substituted, inserted or added. As used herein, "one or plural bases" refers to, for example, 1-300, preferably 1-150, more preferably 1-60, further preferably 1-30, particularly preferably 1-15, bases.

The base sequence shown in SEQ ID NO: 1, 3 or 5 is a base sequence resulting from codon optimization of the gene of *Rhodococcus* sp. D32 strain-derived hydrolase RsD32Est (SEQ ID NO: 2), *Pseudonocardia dioxanivorans* CB1190 strain-derived hydrolase PdEst (SEQ ID NO: 4), or *Microbacterium chocolatum*-derived hydrolase McEst (SEQ ID NO: 6), respectively, for *Escherichia coli* expression. Such DNAs with codons optimized according to the host to be transformed are naturally encompassed in the nucleic acid encoding polypeptide having an activity to catalyze the reaction shown in the above-mentioned formula (1) and usable in the present invention.

The homologue of the nucleic acid of the aforementioned (h) is, for example, a nucleic acid having a base sequence with not less than 60% of sequence identity with the base sequence of SEQ ID NO: 1, 3 or 5, and encoding a polypeptide having an activity to catalyze the reaction shown in the above-mentioned formula (1). Preferably, it is a nucleic acid having a base sequence with a homology (also referred to as an identity) of not less than 80%, more preferably not less than 90%, further preferably not less than 95%, further more preferably not less than 98%, with the base sequence shown in SEQ ID NO: 1, 3 or 5, and encoding a polypeptide having an activity to catalyze the reaction shown in the above-mentioned formula (1).

The homology (to be also referred to as identity) of the base sequences in the present specification can be calculated using homology calculation algorithm NCBI BLAST (National Center for Biotechnology Information Basic Local Alignment Search Tool) and, for example, under the following conditions (expectancy=10; gap allowed; filtering=ON; matching score=1; mismatch score=−3). Similar preferable examples of other algorithm for determining the homology of the base sequence include the above-mentioned homology calculation algorithm of amino acid sequence.

The homologue of the nucleic acid of the aforementioned (h) may be a nucleic acid that hybridizes to the complementary strand of the base sequence of SEQ ID NO: 1, 3 or 5 under stringent conditions as long as it encodes a polypeptide having an activity to catalyze the reaction shown in the above-mentioned formula (1). The "stringent conditions" here can be appropriately determined by reference to the conditions in previous reports (e.g., Current Protocols in Molecular Biology, John Wiley & Sons, 6.3.16.3.6, 1999). Specifically, for example, the conditions include washing once, more preferably 2-3 times, at the salt concentration and temperature corresponding to the washing conditions of general Southern hybridization; 60° C., 1×SSC, 0.1% SDS, preferably, 0.1×SSC, 0.1% SDS, further preferably, 65° C., 0.1×SSC, 0.1% SDS, 68° C., 0.1×SSC, 0.1% SDS etc. (highly stringent conditions), and the like can be mentioned.

Those of ordinary skill in the art can appropriately carry out substitution, deletion, insertion and/or addition to the nucleic acid shown in SEQ ID NO: 1, 3 or 5 by using a site-specific mutagenesis method (Nucleic Acids Res. 10, pp. 6487 (1982), Methods in Enzymol. 100, pp. 448 (1983), Molecular Cloning, PCR A Practical Approach IRL Press pp. 200 (1991)) and the like to introduce the desired mutation, whereby a homologue of the above-mentioned nucleic acid can be obtained.

The nucleic acid of the present invention can encode a polypeptide having an activity to catalyze the reaction shown in the above-mentioned formula (1). When the nucleic acid of the present invention has a base sequence shown in SEQ ID NO: 1, 3 or 5, or a base sequence having high identity with the base sequence shown in SEQ ID NO: 1, 3 or 5, the level of the activity of the hydrolase containing a polypeptide encoded by the nucleic acid to hydrolyze dialkyl 2-vinylcyclopropane-1,1-dicarboxylic acid may be quantitatively equivalent to that of a hydrolase containing a polypeptide having the amino acid sequence shown in SEQ ID NO: 2, 4 or 6, or that containing a polypeptide having the homologue of the amino acid sequence, or may vary within an acceptable range (e.g., about 0.1—about 5 times, preferably about 0.3—about 3 times).

In addition, based on the amino acid sequence shown in SEQ ID NO: 2, 4 or 6 or a part thereof, the base sequence shown in SEQ ID NO: 1, 3 or 5 or a part thereof, it is also possible to perform homology search on, for example, a database such as DNA Databank of JAPAN (DDBJ) and the like to obtain the amino acid sequence information of the polypeptide having an activity to catalyze the reaction shown by the formula (1) or the base sequence information of the DNA encoding the same.

The hydrolase of the present invention has the activity to catalyze the reaction shown by the above-mentioned formula (1) with higher selectivity than the conventionally known hydrolase containing the polypeptide shown in SEQ ID NO: 24. In addition, the hydrolase of the present invention shows low production ratios of (1S,2R) isomer, (1R,2S) isomer and/or (1R,2R) isomer of 1-alkoxycarbonyl-2-vinyl-cyclopropane carboxylic acid when dialkyl 2-vinylcyclopropane-1,1-dicarboxylic acid is hydrolyzed. Particularly, the production ratios of the (1S,2R) isomer, (1R,2S) isomer and/or (1R,2R) isomer are lower than those of a hydrolase containing the polypeptide shown in SEQ ID NO: 24.

In the below-mentioned production method of the present invention, the aforementioned hydrolase may be directly used for the reaction with dialkyl 2-vinylcyclopropane-1,1-dicarboxylic acid; however, it is preferable to use a microorganism or cell capable of producing the enzyme, a treated product of the microorganism or cell, and/or a culture solution containing the enzyme obtained by culturing the microorganism or cell.

As the microorganism or cell having the ability to produce the hydrolase of the present invention, a microorganism or cell that originally has an ability to produce the hydrolase may be used, or a microorganism or cell imparted with the aforementioned producing ability by breeding may be used. The microorganism or cell may be alive or dead and, for example, a quiescent bacterium or the like can be preferably used. Examples of the species of the microorganism or the type of the cell having the ability to produce the hydrolase of the present invention include those described below as the "host microorganism" or "host cell".

As a means for imparting the aforementioned producing ability by breeding, known methods such as a gene recombination treatment (transformation), a mutation treatment and the like can be adopted. As a method of transformation, a method for introducing the DNA of interest, a method of enhancing the expression of a DNA of interest by modifying an expression regulatory sequence such as a promoter on a chromosome, and the like can be mentioned.

Among these, it is preferable to use a microorganism or cell transformed with DNA encoding the aforementioned polypeptide of the present invention.

A nucleic acid (DNA) encoding the polypeptide (hydrolase) of the present invention can be cloned by, as described above, PCR using chromosomal DNA derived from *Rhodococcus* sp. D32 strain, *Pseudonocardia dioxanivorans* CB1190 strain or *Microbacterium chocolatum* as a template, and appropriate primers.

A nucleic acid (DNA) encoding the polypeptide (hydrolase) of the present invention can be cloned by, as described above, preparing full-length hydrolase cDNA directly amplified by RT-PCR using total RNA or mRNA derived from *Rhodococcus* sp. D32 strain, *Pseudonocardia dioxanivorans* CB1190 strain or *Microbacterium chocolatum* as a template, followed by PCR using appropriate primers.

For example, by inserting the DNA encoding the polypeptide of the present invention obtained as mentioned above into a known expression vector in an expressible configuration, the polypeptide gene expression vector of the present invention is provided. Then, by transforming the host cell with the expression vector, a transformant to which a DNA encoding the polypeptide of the present invention is introduced can be obtained. The transformant can also be obtained by expressively incorporating the DNA encoding the polypeptide of the present invention into the chromosomal DNA of the host by a method such as homologous recombination and the like.

In the present specification, the "expression vector" is a genetic element incorporating a polynucleotide encoding a protein having a desired function used for replicating and expressing a protein having a desired function in the aforementioned host organism, by introduction into a host organism. Examples thereof include, but are not limited to, plasmid, virus, phage, cosmid and the like. Preferable expression vector is a plasmid.

In the present specification, the "transformant" means a microorganism or cell into which the gene of interest is introduced using the aforementioned expression vector and the like, and which has acquired an ability to show a desired phenotype associated with a protein having a desired function.

Specifically, as a method for producing a transformant, a method including introducing a DNA encoding the polypeptide of the present invention into a plasmid vector, a phage vector, or a viral vector that is stably present in a host cell, and introducing the constructed expression vector into the host cell, and a method including introducing the DNA directly into the host genome to cause transcription and translation of the genetic information can be mentioned. In this case, it is preferable to join a suitable promoter to the upstream on the 5'-side of the DNA in the host, and it is more preferable to join the terminator to the downstream on the 3'-side. Such promoter and terminator are not particularly limited as long as they are known to function in the cell utilized as the host. For example, the vector, promoter and terminator described in detail in "Basic Course of Microbiology 8 genetic engineering, Kyoritsu Shuppan" can be used.

The host microorganism to be transformed to express the hydrolase of the present invention is not particularly limited as long as the host does not give an adverse influence on dialkyl 2-vinylcyclopropane-1,1-dicarboxylic acid or (1S, 2S)-1-alkoxycarbonyl-2-vinylcyclopropane carboxylic acid. For example, the following microorganisms can be mentioned.

Bacteria with established host vector system belonging to the genera *Escherichia, Bacillus, Pseudomonas, Serratia, Brevibacterium, Corynebacterium, Streptococcus, Lactobacillus* and the like.

Actinomycetes with established host vector system belonging to the genera *Rhodococcus, Streptomyces* and the like.

Yeast with established host vector system belonging to the genera *Saccharomyces, Kluyveromyces, Schizosaccharomyces, Zygosaccharomyces, Yarrowia, Trichosporon, Rhodosporidium, Hansenula, Pichia, Candida* and the like.

Molds with established host vector system belonging to the genera *Neurospora, Aspergillus, Cephalosporium, Trichoderma* and the like.

The procedure for preparing the transformant, the construction of the recombinant vector suitable for the host, and the method for culturing the host can be performed according to the techniques conventionally used in the fields of molecular biology, biotechnology, and genetic engineering (e.g., the method described in Molecular Cloning).

Specific examples of a preferred host microorganism, a preferred transformation method in each microorganism, vector, promoter, terminator, and the like are recited in the following; however, the present invention is not limited to these examples.

In *Escherichia*, particularly *Escherichia coli*, the plasmid vector includes, for example, pBR, pUC series plasmids and the like, and promoters derived from lac (β-galactosidase), trp (tryptophan operon), tac, trc (fusion of lac, trp), λ phage PL, PR and the like, and the like. The terminator includes, for example, terminators derived from trpA, derived from phage, derived from rrnB ribosomal RNA and the like.

In *Bacillus*, the vector includes, for example, pUB110 series plasmids, pC194 series plasmids and the like, which may also be integrated with the chromosome. As the promoter and terminator, promoters and terminators of enzyme gene such as alkaline protease, neutral protease, α-amylase and the like, and the like can be utilized.

In *Pseudomonas*, the vector includes, for example, general host vector systems established in *Pseudomonas putida, Pseudomonas cepacia* and the like, a plasmid relating to the decomposition of a toluene compound, broad host range vector based on TOL plasmid (including gene necessary for autonomous replication derived from RSF1010 and the like) pKT240 (Gene, 26, 273-82 (1983)) and the like.

In *Brevibacterium*, particularly *Brevibacterium lactofermentum*, the vector includes, for example, plasmid vectors such as pAJ43 (Gene 39, 281 (1985)) and the like. As the promoter and terminator, various promoters and terminators used in *Escherichia coli* can be used.

In *Corynebacterium*, particularly *Corynebacterium glutamicum*, the vector includes, for example, plasmid vectors such as pCS11 (JP-A-57-183799), pCB101 (Mol. Gen. Genet. 196, 175 (1984)) and the like.

In *Saccharomyces*, particularly *Saccharomyces cerevisiae*, the vector includes, for example, YRp series, YEp series, YCp series, YIp series plasmid and the like. In addition, promoters and terminators of various enzyme genes such as alcohol dehydrogenase, glyceraldehyde-3-phosphate dehydrogenase, acidic phosphatase, β-galactosidase, phosphoglycerate kinase, enolase can be used.

In *Schizosaccharomyces*, the vector includes, for example, plasmid vectors derived from *Schizosaccharomyces pombe* described in Mol. Cell. Biol. 6, 80 (1986) and the like. Particularly, pAUR224 is commercially available from Takara Bio Inc. and can be utilized with ease.

In *Aspergillus, Aspergillus niger, Aspergillus oryzae* and the like are most studied well among molds, integrations into plasmids and chromosomes are available, and promoters derived from extracellular proteases and amylase can be used (Trends in Biotechnology 7, 283-287 (1989)).

In addition to the above, host vector systems corresponding to various microorganisms have been established, and they can be used as appropriate.

In addition to microorganisms, various host/vector systems have been established in plants and animals. Particularly, a system for expressing a large amount of heterologous protein in animals such as insect (e.g., silkworm) and the like (Nature 315, 592-594 (1985)), plants such as *Brassica*, corn, potato and the like, and a system using *Escherichia coli* cell-free extract and a cell-free protein synthesis system of wheat germ and the like has been established, and they can be preferably utilized.

Examples of the treated product of a microorganism or cell having an ability to produce the hydrolase of the present invention include preparations such as the microorganism or cell treated with an organic solvent such as acetone, dimethyl sulfoxide (DMSO), toluene or the like, or a surfactant, or freeze-dry treated, or physically or enzymatically disrupted, or the like, an enzyme fraction in the microorganism or cell which was obtained as a crude product or purified product, and further, those immobilized on a carrier represented by polyacrylamide gel, carageenan gel or the like, and the like.

Examples of the culture solution containing the enzyme obtained by culturing a microorganism or cell having the ability to produce the hydrolase of the present invention include a suspension of the cell and a liquid medium and, when the cell is a type with secretory expression, a supernatant obtained by removing the cell by centrifugation or the like or a concentrate thereof.

2. Composition of the Present Invention

The composition (enzymatic agent) of the present invention contains the hydrolase of the present invention, a microorganism or cell having an ability to produce the enzyme, a treated product of the microorganism or cell, and/or a culture solution containing the enzyme obtained by culturing the microorganism or cell, and catalyzes a reaction to produce (1S,2S)-1-alkoxycarbonyl-2-vinylcyclopropane carboxylic acid by using dialkyl 2-vinylcyclopropane-1,1-dicarboxylic acid as a substrate. Using the composition of the present invention as a catalyst, optically highly pure (1S,2S)-1-alkoxycarbonyl-2-vinylcyclopropane carboxylic acid can be industrially produced with high efficiency at low costs, and the composition is useful.

The composition of the present invention may contain excipient, buffering agent, suspension, stabilizer, preservative, antiseptic, saline and the like in addition to the active ingredient (enzyme, etc.). As the excipient, lactose, sorbitol, D-mannitol, sucrose and the like can be used. As the buffering agent, phosphate, citrate, acetate and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, benzalkonium chloride, p-hydroxybenzoic acid, chlorobutanol and the like can be used.

3. Production of Carboxylic Acid Monoester Represented by the Following Formula (II') by Using the Hydrolase of the Present Invention According to the present invention, production shown by the formula (2), namely, a production method of a carboxylic acid monoester represented by the following formula (II'), including reacting the hydrolase of the present invention with a dicarboxylic acid ester represented by the following formula (I') to produce a carboxylic acid monoester represented by the following formula (II'), is provided.

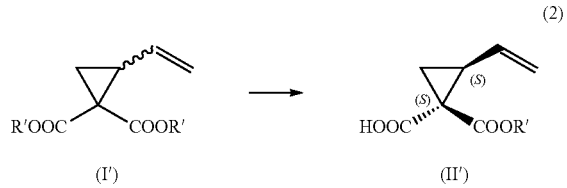

(2)

wherein R' is an optionally substituted alkyl group having 1-10 carbon atoms, an aralkyl group having 7-20 carbon atoms, or an aryl group having 6-12 carbon atoms.

In the formula (2), the "alkyl group with 1-10" of the "optionally substituted alkyl group having 1-10 carbon atoms" for R' is, for example, a linear or branched or cyclic alkyl group having 1-10 carbon atoms, more preferably a linear or branched or cyclic alkyl group having 1-6 carbon atoms. Of these, for example, a methyl group, an ethyl group, an isopropyl group, a normal propyl group, a normal butyl group, an isobutyl group, a sec-butyl group, a tert-butyl group, a normal pentyl group, an isopentyl group, a tert-pentyl group, a neopentyl group, a normal hexyl group, a cyclopropyl group, a cyclobutyl group, a cyclopentyl group, a cyclohexyl group and the like are preferable, an alkyl group having 1-4 carbon atoms is more preferable, a linear or branched alkyl group having 1-4 carbon atoms is further preferable, and an ethyl group is particularly preferable. The substituent of the "optionally substituted alkyl group having 1-10 carbon atoms" is, for example, a halogen atom (e.g., chlorine atom, bromine atom), a linear or branched alkoxy group having 1-6 carbon atoms (e.g., methoxy, ethoxy), a nitro group or the like.

The "aralkyl group having 7-20 carbon atoms" of the "optionally substituted aralkyl group having 7-20 carbon atoms" for R' is, for example, preferably an aralkyl group having 7-12 carbon atoms. Of these, a benzyl group, a 2-phenylethyl group, a 1-phenylethyl group, a 3-phenylpropyl group and the like can be mentioned. The substituent of the "optionally substituted aralkyl group having 7-20 carbon atoms" is, for example, a halogen atom (e.g., chlorine atom, bromine atom), a linear or branched alkyl group having 1-6 carbon atoms (e.g., methyl, ethyl), a linear or branched alkoxy group having 1-6 carbon atoms (e.g., methoxy, ethoxy) or the like. The substituent of the "optionally substituted aralkyl group having 7-20 carbon atoms" is, for example, preferably a benzyl group, a 4-methylbenzyl group, a 4-methoxybenzyl group, a 4-chlorobenzyl group, a 4-bromobenzyl group, a 2-phenylethyl group, a 1-phenylethyl group, a 3-phenylpropyl group or the like.

The "aryl group having 6-12 carbon atoms" of the "optionally substituted aryl group having 6-12 carbon atoms" for R' is, for example, a phenyl group, a 1-naphthyl group, a 2-naphthyl group or the like. The substituent of the "optionally substituted aryl group having 6-12 carbon atoms" is, for example, a halogen atom (e.g., chlorine atom, bromine atom), a linear or branched alkyl group having 1-6 carbon atoms (e.g., methyl, ethyl), a linear or branched alkoxy group having 1-6 carbon atoms (e.g., methoxy, ethoxy), a nitro group or the like. Preferable examples of the "optionally substituted aryl group having 6-12 carbon atoms "include phenyl group, 1-naphthyl group, 2-naphthyl group, o-methylphenyl group, m-methylphenyl group, p-methylphenyl group, o-methoxyphenyl group, m-methoxyphenyl group, p-methoxyphenyl group, 2,3-dimethylphenyl group, 2,4-dimethylphenyl group, 2,5-dimethylphenyl group, 2,6-dimethylphenyl group, 3,4-dimethylphenyl group, 3,5-dimethylphenyl group, 2,3,5-trimethylphenyl group, 2,3,6-trimethylphenyl group, 2,4,6-trimethylphenyl group, o-nitrophenyl group, m-nitrophenyl group, p-nitrophenyl group and the like.

R' is particularly preferably a methyl group, an ethyl group, a tert-butyl group, or a benzyl group, more preferably an ethyl group.

The two R' in the formula (I') may be the same or different, and are preferably the same.

When the hydrolase of the present invention is contacted with a dicarboxylic acid diester represented by the formula (I'), the purified or crudely purified hydrolase of the present invention, a microorganism or cell having an ability to produce the hydrolase of the present invention (e.g., transformant having DNA encoding the polypeptide of the present invention, etc.), a treated product of the microorganism or cell, and/or a culture solution containing the enzyme obtained by culturing the microorganism or cell are/is contacted with the dicarboxylic acid diester represented by the formula (I'), whereby the carboxylic acid monoester represented by the formula (II') can be produced.

The hydrolase of the present invention may be directly used for the reaction. Use of a microorganism or cell having an ability to produce the enzyme, a treated product of the microorganism or cell, and/or a culture solution containing the enzyme obtained by culturing the microorganism or cell is preferable. Among these, use of a transformant having DNA encoding the polypeptide of the present invention is preferable.

As the amount of the microorganism or cell to be added to the reaction mixture, a treated product of the microorganism or cell, and/or a culture solution containing the enzyme obtained by culturing the microorganism or cell is added such that the concentration of the microorganism or cell in the reaction mixture is generally about 0.1 w/v %-50 w/v %, preferably 1 w/v %-20 w/v %, in wet body weight when a microorganism or cell has been added. When a treated product and a culture solution are used, the specific activity of the enzyme is determined, and they are added to achieve the above-mentioned cell concentration. As used herein, w/v % means weight/volume %.

As the dicarboxylic acid diester represented by the formula (I') which is a reaction substrate of the hydrolase of the present invention, (2S) isomer or racemate is generally used.

The reaction method is not particularly limited, and a dicarboxylic acid diester represented by the formula (I') to be the substrate is added to a liquid containing the hydrolase of the present invention, and they are reacted at a suitable temperature and a suitable pressure (e.g., about atmospheric pressure). In this way, a carboxylic acid monoester represented by the formula (II') can be produced.

A dicarboxylic acid diester to be a reaction substrate and represented by the formula (1') is generally used at a substrate concentration of 0.01 w/v %-90 w/v %, preferably 0.1 w/v %-30 w/v. A reaction substrate may be added at once at the start of the reaction. When the enzyme is inhibited by the substrate, the enzyme is desirably added continuously or intermittently to reduce the influence thereof or improve accumulation concentration of the resultant product.

The reaction is generally performed in an aqueous medium or a mixture of the aqueous medium and an organic solvent. Examples of the aqueous medium include water and buffer. As the organic solvent, one showing high solubility of the dicarboxylic acid diester represented by the formula (I') which is the reaction substrate, such as methanol, ethanol, 1-propanol, 2-propanol, 1-butanol, tert-butanol, acetone, dimethyl sulfoxide and the like can be used. As the organic solvent, ethyl acetate, butyl acetate, toluene, chloroform, n-hexane and the like which are effective for removing reaction by-products and the like can also be used.

The reaction is generally performed at a reaction temperature of 4° C.-60° C., preferably 10° C.-45° C., generally under the conditions of pH 3-11, preferably pH 5-8. The reaction time is generally about 1 hr-72 hr.

After completion of the reaction, the carboxylic acid monoester represented by the formula (II') which is produced by the production method of the present invention can be separated by a separation or purification method known to those of ordinary skill in the art, such as centrifugation, membrane treatment, or the like of fungus/bacterium, protein and the like in the reaction mixture after which purified by appropriately combining extraction with organic solvents such as 1-butanol, tert-butanol and the like, distillation, column chromatography using ion exchange resin, silica gel, etc., crystallization at the isoelectric point, crystallization with monohydrochloride, dihydrochloride, calcium salt, etc., and the like.

The hydrolase of the present invention can be particularly preferably used for a method for producing (1S,2S)-1-ethoxycarbonyl-2-vinylcyclopropane carboxylic acid by hydrolyzing diethyl 2-vinylcyclopropane-1,1-dicarboxylic acid.

The dicarboxylic acid diester represented by the formula (I') as a substrate can be produced by the following reaction of the formula (3).

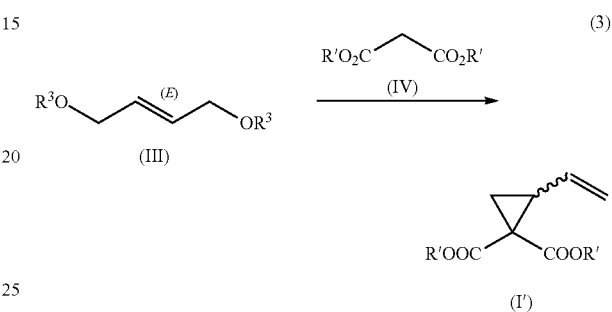

wherein $R^3$ is an optionally substituted arylsulfonyl group having 6-12 carbon atoms, an optionally substituted alkylsulfonyl group having 1-10 carbon atoms, or an optionally substituted aralkylsulfonyl group having 7-20 carbon atoms, and R' is as defined above.

That is, it can be produced by reacting a compound represented by the formula (III) with a malonic acid ester represented by the formula (IV) in the presence of alkali metal alkoxide or alkali metal hydride.

Examples of the "arylsulfonyl group having 6-12 carbon atoms" of the "optionally substituted arylsulfonyl group having 6-12 carbon atoms" for $R^3$ in the formula (III) include benzenesulfonyl group, 1-naphthalenesulfonyl group, 2-naphthalenesulfonyl group and the like. Examples of the "alkylsulfonyl group having 1-10 carbon atoms" of the "optionally substituted alkylsulfonyl group having 1-10 carbon atoms" include methanesulfonyl group, ethanesulfonyl group, propanesulfonyl group and the like. Examples of the "aralkylsulfonyl group having 7-20 carbon atoms" of the "optionally substituted aralkylsulfonyl group having 7-20 carbon atoms" include benzylsulfonyl group and the like. The substituent of the "optionally substituted arylsulfonyl group having 6-12 carbon atoms", the "optionally substituted alkylsulfonyl group having 1-10 carbon atoms" and the "optionally substituted aralkylsulfonyl group having 7-20 carbon atoms" is, for example, a halogen atom (e.g., chlorine atom, bromine atom), linear or branched alkyl group having 1-6 carbon atoms (e.g., methyl, ethyl), linear or branched alkoxy group having 1-6 carbon atoms (e.g., methoxy, ethoxy), nitro group or the like. Specific preferable examples of $R^3$ include benzenesulfonyl group, p-toluenesulfonyl group, 1-naphthalenesulfonyl group, 2-naphthalenesulfonyl group, methanesulfonyl group, ethanesulfonyl group, propanesulfonyl group, trifluoromethanesulfonyl group, and benzylsulfonyl group and the like. $R^3$ is preferably a methanesulfonyl group, a benzenesulfonyl group or a p-toluenesulfonyl group, particularly preferably a p-toluenesulfonyl group.

A compound represented by the formula (III) which is a starting compound of the formula (3) can be produced according to a known method, for example, the method described in Frederic Dolle et al., Bioorg. Med. Chem. 2006, 14, 1115-1125 or the like. It can also be produced by the following reaction of the formula (4).

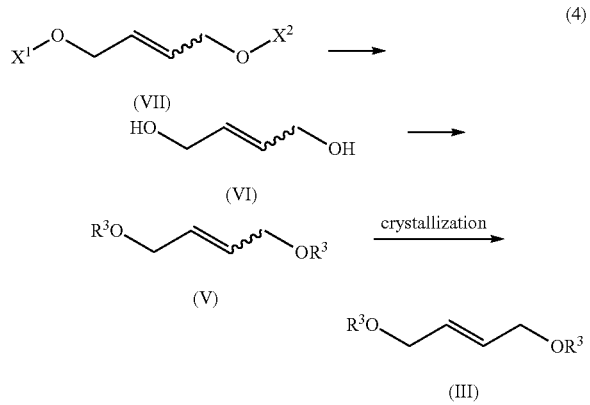

That is, it can be produced by reacting 1,4-butenediol (VI) with $R^3X$ (X is a halogen atom such as a chlorine atom, a bromine atom, an iodine atom or the like), and crystallizing the obtained compound of the formula (V), or hydrolyzing commercially available starting compound (VII) with an acid or base to give 1,4-butenediol, reacting same with $R^3X$, and crystallizing the obtained compound of the formula (V).

In the formula (4), $X^1$ is a hydrogen atom or $R^1$, $X^2$ is a hydrogen atom or $R^2$, $R^1$ and $R^2$ are each independently an alkylcarbonyl group having 2-11 carbon atoms, an aralkylcarbonyl group having 8-21 carbon atoms, or an arylcarbonyl group having 7-13 carbon atoms, provided that $X^1$ and $X^2$ are not simultaneously hydrogen atoms. Preferably, $X^1$ is $R^1$, and $X^2$ is $R^2$, more preferably $R^1$ and $R^2$ are both acetyl groups, ethylcarbonyl groups, tert-butylcarbonyl groups, or benzoyl groups, further preferably acetyl groups, since they are commercially available as products on the market.

Using the carboxylic acid monoester represented by the formula (II') obtained in the present invention, (1R,2S)-1-amino-1-ethoxycarbonyl-2-vinylcyclopropane (VIII) and a salt thereof which are useful intermediates for the production of various HCV NS3 protease inhibitors and the like under development as therapeutic agents for hepatitis C can be produced. Furthermore, by producing using the thus-obtained carboxylic acid monoester represented by the formula (II'), optically highly pure (1R,2S)-1-amino-1-alkoxycarbonyl-2-vinylcyclopropane can also be produced with high efficiency at low costs.

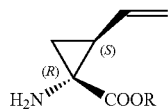

While the present invention is explained in further detail in the following by referring to Examples, the present invention is not limited thereto.

EXAMPLE

Example 1: Cloning of Hydrolase Gene

Rhodococcus sp. D32 strain was obtained by exploring soil samples using hydrolytic activity as an index. A new hydrolase RsD32Est (SEQ ID NO: 2) was obtained from the analysis of the hydrolase produced by this microorganism and the analysis of gene information. Based on this amino acid sequence information, a codon-optimized gene sequence (SEQ ID NO: 1) for Escherichia coli expression encoding RsD32Est was artificially synthesized by DNA2.0 Inc. to obtain pJ411RsD32Est.

Codon-optimized gene sequences (pedst_Ecodon, SEQ ID NO: 3, mcest_Ecodon, SEQ ID NO: 5 and afx20780_Ecodon) for Escherichia coli expression that encode Pseudonocardia dioxanivorans CB1190 strain, Microbacterium chocolatum-derived putative hydrolase PdEst (GenBank Accession No. WP 01367363, SEQ ID NO: 4), McEst (GenBank Accession No. WP_053548180, SEQ ID NO: 6) and hydrolase AFX20780 (GenBank Accession No. AFX20780, SEQ ID NO: 8) were artificially synthesized by DNA2.0 Inc. and inserted into pJExpress411 (manufactured by DNA2.0 Inc.) to produce plasmids (pJ411PdEst, pJ411 McEst and pJ411AFX20780, respectively). The amino acid sequences encoded by the gene sequences were named as RsD32Est, PdEst, McEst, AFX20780, respectively. Respective amino acid sequences are shown in SEQ ID NO: 2 (RsD32Est), SEQ ID NO: 4 (PdEst), SEQ ID NO: 6 (McEst), and SEQ ID NO: 8 (AFX20780).

Using each of the obtained plasmids, Escherichia coli BL21 (DE3) (manufactured by Invitrogen Corp.) was transformed according to a conventional method, and recombinant Escherichia coli BL21(DE3)/pJ411RsD32Est, BL21 (DE3)/pJ411PdEst, BL21(DE3)/pJ411 McEst and BL21 (DE3)/pJ411AFX20780 were obtained. To obtain bacteria expressing the introduced gene, each recombinant Escherichia coli was cultured at 30° C. using a liquid LB medium containing kanamycin and a lac promoter inducer, and the bacteria were harvested after the culture for about 20 hr.

Escherichia coli clone No. 26 prepared in Reference Example 1 described later was also cultured at 30° C. using a liquid LB medium containing kanamycin and a lac promoter inducer, and harvested after the culture for about 20 hr.

Example 2

Using each of the bacteria obtained in Example 1, reaction was performed in 100 mmol/L potassium phosphate buffer containing 30 g/L of racemic diethyl 2-vinylcyclopropane-1,1-dicarboxylic acid (hereinafter to be referred to as VCPDE) and 5% dimethyl sulfoxide at a condition of 30° C., pH 7 for 21 hr. As each bacterium, the bacterium obtained by centrifugation from 0.4 mL of the culture solution prepared in Example 1 was used. VCPDE was synthesized according to the method described in the Synthesis Example of JP-B-5657560.

The reaction solution after the reaction for 20 hr was diluted with acetonitrile to an appropriate concentration and analyzed by high performance liquid chromatography (HPLC) under the following conditions. Analysis conditions (1) are analysis conditions for evaluating optical purity. Analysis conditions (2) are analysis conditions for quantifying the Anti isomer containing the (1S,2S) isomer of the produced 1-ethoxycarbonyl-2-vinylcyclopropanecarboxylic acid as the main component and evaluating the production rate of Syn isomer relative to Anti isomer.

Analysis Conditions (1)
    column: CHIRALPAK AD-3 (4.6×250 mm, manufactured by Daicel chemical)
    eluent: hexane:ethanol:trifluoroacetic acid=95:5:0.1
    flow rate: 0.8 ml/min temperature: 30° C.
detection: UV 210 nm
Analysis Conditions (2)
    column: COSMOSIL 5C18-MS-II (4.6×250 mm, manufactured by Nacalai Tesque)
    eluent A: 0.1% trifluoroacetophenone-containing aqueous solution
    eluent B: 0.1% trifluoroacetophenone-containing acetonitrile
    flow rate: 0.8 ml/min
    temperature: 40° C.
    detection: UV 210 nm

TABLE 1

| Gradient program | | |
| --- | --- | --- |
| min | eluent A (%) | eluent B (%) |
| 0 | 75 | 25 |
| 20 | 30 | 70 |
| 23 | 30 | 70 |
| 30 | 75 | 25 |

Table 1 shows the amount of Anti isomer of 1-ethoxycarbonyl-2-vinylcyclopropane carboxylic acid produced using each bacterium, ratio of Syn isomer to Anti isomer in the product, and optical purity.

TABLE 2

| amino acid sequence | Anti isomer (g/L) | ratio of Syn isomer to Anti isomer in the product (%) | optical purity (% e.e.) |
| --- | --- | --- | --- |
| RsD32Est | 13.6 | not detected | 99.1 |
| PdEst | 4.28 | not detected | 80.9 |
| McEst | 4.71 | 0.2 | 64.4 |
| AFX20780 | 2.71 | 0.5 | −45.9 |
| PnbA3027-m26 | 2.69 | 14.2 | 99.0 |

As is clear from Table 2, the hydrolase of the present invention having the amino acid sequences shown in SEQ ID NO: 2 (RsD32Est), SEQ ID NO: 4 (PdEst) and SEQ ID NO: 6 (McEst) produces a higher amount of Anti isomer of 1-ethoxycarbonyl-2-vinylcyclopropane carboxylic acid than the conventional hydrolase having the amino acid sequences shown in SEQ ID NO: 8 (AFX20780) and SEQ ID NO: 24 (PnbA3027-m26), and shows low production rate of Syn isomer relative to Anti isomer.

Particularly, the hydrolase of the present invention having the SEQ ID NO: 2 (RsD32Est) produces an extremely high amount of Anti isomer of 1-ethoxycarbonyl-2-vinylcyclopropane carboxylic acid, does not produce Syn isomer, and shows extremely high optical purity.

Figure 2:
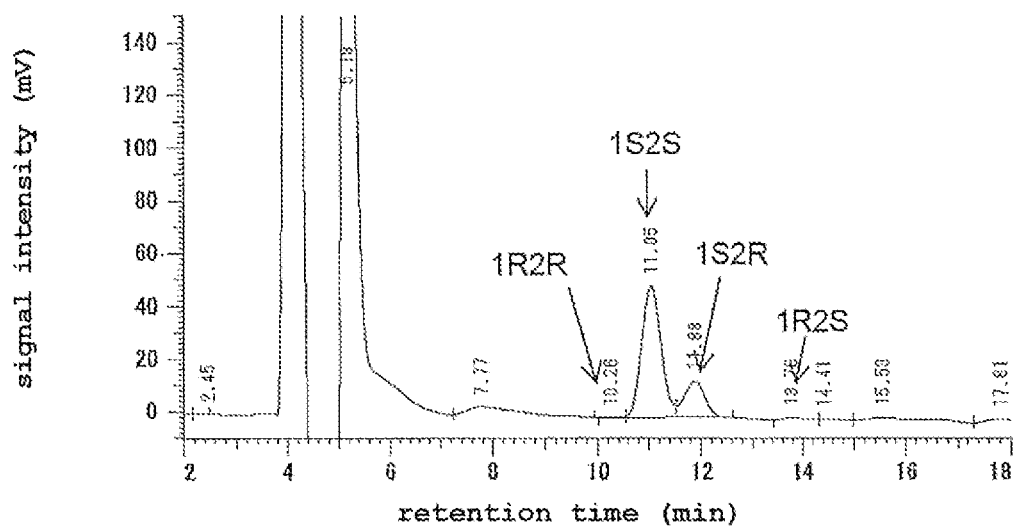
FIG. 2 shows HPLC analysis results of the reaction product obtained using a bacterium having the amino acid sequence PnbA3027-m26.

FIG. 1 shows HPLC analysis results of the reaction product obtained using a bacterium having the amino acid sequence RsD32Est, and FIG. 2 shows HPLC analysis results of the reaction product obtained using a bacterium having the amino acid sequence PnbA3027-m26. As is clear from FIG. 1, the hydrolase of the present invention having the amino acid sequence RsD32Est scarcely produces (1S, 2R) isomer, (1R,2S) isomer or (1R,2R) isomer of 1-ethoxycarbonyl-2-vinylcyclopropane carboxylic acid, and can produce (1S,2S) isomer with high selectivity. As is clear from FIG. 2, conventional hydrolase having the amino acid sequence PnbA3027-m26 shows high production of (1S,2R) isomer of 1-ethoxycarbonyl-2-vinylcyclopropane carboxylic acid, and low selectivity as compared to the hydrolase of the present invention.

Example 3: Production of (1S,2S)-1-Ethoxycarbonyl-2-Vinylcyclopropane Carboxylic Acid 1 mol/L potassium phosphate buffer (pH 7.0) (160 mL), desalting water (1332 mL), diethyl 2-vinylcyclopropane-1, 1-dicarboxylic acid (84.2 g) and wet bacteria (24 g) of Escherichia coli clone BL21(DE3)/pJ411RsD32Est obtained in Example 1 were mixed in a 5 L jar fermentor, and reaction was performed for 24 hr under a sufficient stirring speed at a reaction temperature 30° C. and pH 7.0 during the reaction. The concentration of (1S,2S)-1-ethoxycarbonyl-2-vinylcyclopropane carboxylic acid at the reaction end-point was 22.3 g/L.

Bacteria and bacterial debris were removed from the reaction solution (1100 mL) (pure content of (1S,2S)-1-ethoxycarbonyl-2-vinylcyclopropane carboxylic acid was 22.2 g) after completion of the reaction, toluene (500 mL) was added, and the mixture was stirred at room temperature for 20 min. The toluene layer was separated and the remaining diethyl 2-vinylcyclopropane-1,1-dicarboxylic acid was removed. The pH of the obtained aqueous layer was adjusted to 2.0 by adding 6 N(=3 mol/L) sulfuric acid. Thereafter, toluene (250 mL) was added, and the mixture was stirred at room temperature for 20 min, and a toluene layer containing (1S,2S)-1-ethoxycarbonyl-2-vinylcyclopropane carboxylic acid was obtained. To the obtained aqueous layer was added again toluene (250 mL), and the mixture was stirred at room temperature for 20 min and a toluene layer containing (1S,2S)-1-ethoxycarbonyl-2-vinylcyclopropane carboxylic acid was obtained. As a result of the purity analysis and optical purity analysis of the obtained toluene layer by HPLC analysis, the pure content of (1S,2S)-1-ethoxycarbonyl-2-vinylcyclopropane carboxylic acid was 19.3 g and the optical purity was 99.7% e.e.

Reference Example 1: Cloning of Paranitrobenzyl Esterase Gene (pnbA3027; SEQ ID NO: 9)

Gene Cloning

Chromosome DNA was prepared from the bacteria obtained by culturing Bacillus subtilis NBRC3027 overnight in a liquid medium designated by the strain storage organization and using the DNeasy Blood & Tissue Kit (manufactured by QIAGEN).

Primers to amplify the full length of the paranitrobenzyl esterase gene were designed and synthesized based on the gene sequence (pnbA23857, SEQ ID NO: 11) encoding paranitrobenzyl esterase (PNBE23857, GenBank Accession No. AQR87688, SEQ ID NO: 12) derived from Bacillus subtilis strain ATCC23857 of known genomic sequences. Respective base sequences are shown in SEQ ID NOs: 13 (pnbA F) and 14 (pnbA R) in the Sequence Listing.

Using the prepared chromosomal DNA as a template, and pnbA F, pnbA R as primers, about 1.5 kbp DNA fragment was amplified by PCR.

Preparation of Expression Vector

Using plasmid pKV32 prepared according to the method described in JP-A-2005-34025 as a template, and the primer (pKVXmaIFW) shown in SEQ ID NO: 15 and the primer (pKVXmaIRV) shown in SEQ ID NO: 16, about 4 kbp fragment was amplified by PCR. The amplified fragment was digested with XmaI, self-closed with the Ligation- Convenience Kit (manufactured by NIPPON GENE Co. Ltd.), and the resulting plasmid was named pKW32.

Preparation of Expression Plasmid

The DNA fragment obtained by the aforementioned gene cloning was introduced according to a conventional method into the cloning vector pKW32 prepared in the aforementioned "Preparation of expression vector". In the following, the obtained plasmid is indicated as ppnbA3027.

The DNA sequence inserted into the plasmid was analyzed and confirmed to contain a gene consisting of 1467 bp ORF. The obtained gene was named pnbA3027 and the sequence is shown in SEQ ID NO: 9. The amino acid sequence encoded by this DNA sequence was named PNBE3027, and the amino acid sequence thereof is shown in SEQ ID NO: 10. The amino acid sequence of PNBE3027 showed 90% sequence identity to the sequence of known PNBE23857.

Reference Example 2: Alteration of Paranitrobenzyl Esterase Gene by Mutation Introduction Using plasmid ppnbA3027 obtained in Reference Example 1 as a template, and the primer (L70FW) shown in SEQ ID NO: 17 and the primer (L70RV) shown in SEQ ID NO: 18 in the Sequence Listing, a random mutation was introduced into the bases encoding leucine at amino acid number 70 by QuikChange Multi Site-Directed Mutagenesis Kit (manufactured by Stratagene Corp.). Similarly, using the primer (L313FW) shown in SEQ ID NO: 19 and the primer (L313RV) shown in SEQ ID NO: 20 in the Sequence Listing, a random mutation was introduced into the bases encoding leucine residue at amino acid number 313. In addition, using the primer (L270 L273FW) shown in SEQ ID NO: 21 and the primer (L270 L273RV) shown in SEQ ID NO: 22 in the Sequence Listing, a random mutation was introduced into the bases encoding leucine residues at amino acid numbers 270 and 273. Using the obtained mutation-introduced plasmid, *Escherichia coli* JM109 (manufactured by Takara Bio Inc.) was transformed according to a conventional method.

Clone No. 26 was isolated from the obtained recombinant *Escherichia coli*, and the DNA sequence inserted into the plasmid possessed by this clone was analyzed. As a result, the sequence thereof (named pnbA3027-26) was as shown in SEQ ID NO: 23. The amino acid sequence encoded by this DNA sequence was named PNBE3027-m26, and the amino acid sequence thereof is shown in SEQ ID NO: 24.

INDUSTRIAL APPLICABILITY

Using the hydrolase of the present invention and the like, optically highly pure (1S,2S)-1-alkoxycarbonyl-2-vinylcyclopropane carboxylic acid can be industrially produced with high efficiency at low costs.

The present invention is based on patent application No. 2018-070188 filed in Japan, the contents of which are encompassed in full herein.

SEQUENCE LISTING

```
Sequence total quantity: 24
SEQ ID NO: 1              moltype = DNA  length = 1062
FEATURE                   Location/Qualifiers
misc_feature              1..1062
                          note = Ecoli opt
source                    1..1062
                          mol_type = other DNA
                          organism = synthetic construct
SEQUENCE: 1
atgaatctgc caccgggtgt ccgctctgtt acgactcaaa cttcacgtct gcgcttgcat    60
cacttggagg ccggtccggt cgatggcgtg ccactggttc tggtgcacgg taatctgagc   120
tccggtcgtt tctatgaaga tgtgatgccg gccctcgcga aaacctatcg cgtcatcgca   180
ccggatatgc gcggtttcgg tgatagcgag cgcgttaccc tggatgcgac gcgcggtctg   240
gcggactggg cagatgacat tgcggcgctg ctggaagcgt tagacattga ccaggctccg   300
catctgctgg gctggagcac gggtgcaggc gcgattaccc gttacgtcct ggatggtcgt   360
accgccgctt cgctgacgtt gatggacccg gtcccgccgt acggtttcgt cggtatgcac   420
gcagacggca cgccgtggtt tagcgactat gcgggctgtg gtgctggtgt aatgaacacg   480
gaatttaccg agcgtattgc tgctggtgac cgttccaccg attccctggc atctccgcgt   540
aacgttgcgg caggcttttg gggtgaggcg ccgccgatca gccaagagcg tgttgacgtg   600
ctgattacg agctgttgaa aacctgggtt agcgaagata attttccggg tagcgttgtg   660
ccgagcaaaa actggccggg tatcgcccct ggcaccaccg gcatcctgaa cgcactgagc   720
ccgaagtact gcgactggag ccgcatcacc gagctgggta gcaagccgcc gattatgtgg   780
atccagggtg gccaagatga tgtgatcagc aatgcgagcc acaacgaccc ggcgaccctg   840
ggcgcagcgg gcctgatccc gggttggccg ggcgaagatg tctgcccggc gcagccgatg   900
atcacccaga ttcgtgatgt gttgcaagca tacgaagatg ccggcggccg tacgcgtacc   960
gagtggttcg aggcaagcca ccatctgcct atgattgaag aaccggaccg ttggctgcaa  1020
gccgtgtcta gctttgtggc ggaagccgac gcgattcgt aa                      1062

SEQ ID NO: 2              moltype = AA  length = 353
FEATURE                   Location/Qualifiers
source                    1..353
                          mol_type = protein
                          note = strain D32
                          organism = Rhodococcus sp.
SEQUENCE: 2
MNLPPGVRSV TTQTSRLRLH HLEAGPVDGV PLVLVHGNLS SGRFYEDVMP ALAKTYRVIA   60
PDMRGFGDSE RVTLDATRGL ADWADDIAAL LEALDIDQAP HLLGWSTGAG AITRYVLDGR  120
TAASLTLMDP VPPYGFVGMH ADGTPWFSDY AGCGAGVMNT EFTERIAAGD RSTDSLASPR  180
NVAAGFWGEA PPISQERVDV LIDELLKTWV SEDNFPGSVV PSKNWPGIAP GTTGILNALS  240
PKYCDWSRIT ELGSKPPIMW IQGGQDDVIS NASHNDPATL GAAGLIPGWP GEDVCPAQPM  300
ITQIRDVLQA YEDAGGRTRT EWFEASHHLP MIEEPDRWLQ AVSSFVAEAD AIA         353
```

```
SEQ ID NO: 3           moltype = DNA  length = 1053
FEATURE                Location/Qualifiers
misc_feature           1..1053
                       note = Ecoli opt
source                 1..1053
                       mol_type = other DNA
                       organism = synthetic construct
SEQUENCE: 3
atgcagctgt tgcctggtgt tcgtagcgtg gtggtcccaa ctgatcgtct ggaagttcat      60
ttggtggagt atggtcctga agagggcgtt ccggttgtga tgctgcacgg taaccttttct   120
accggtcgtt tctttgagca cctgttcccg ggtgccccgc agggttaccg tatcatcgca    180
ccggacatgc gttgctttgg cgatacggaa cgtctgccgt tagacgcaac ccgtggcctg    240
gctgactggg ccgatgacgt tgccgctctg cgtgtgcgtg agccggttca gcgtccggtt    300
cacctcctgg gctggagcac tgcgggcgcg ccattgtgg attttgcaag cgcgcatccg     360
gtcacctctc tgaccttcct ggatccggtc agcccgtacg gttttggtgg cgtgctggcg    420
gatggtacgc cgtgcttccc ggactttgcc ggttccggcg gcggcattgt gaatccagaa    480
gtcgtccgtc gcctggccga gggtgacgat acgaccgaga gcccgttttc tattcgcagc    540
gtcatgcgtg gctcgtattg gttggaaagc catagcgaac cgcgcgaaga tctgctggta    600
gcagaagtgc tgaaaaccgt gaccggcgac gacaattatc ctggtgactc cgtcgcgagc    660
ccgaattggc cgggtagcgc accgggtacg accggtatca tcaacgctct gagcccgaag    720
tactgtaact ggacgcgcgt tgttgacctg gatccgaaac cgccgttttt gtggacgcat    780
ggtgccgagg acaccgtcgt cgcggatgcg agcatgcaag acctgggtac cctgggcgag    840
ctgggttacg tgccgggctg gccgggtgca gatgtgttcc cgagccagcc gatggtgagc    900
caaattcgcg aagtcctggg ccgttacgcg gcggcgggtg gccacgttcg caccgagatc    960
ctgccgggtg cgggccactc cccgcacatt gagctgccag aactgtggag cggtgtgttt   1020
tgggacttcg ttggtgcggc ggagcgtggt taa                                1053

SEQ ID NO: 4           moltype = AA  length = 350
FEATURE                Location/Qualifiers
source                 1..350
                       mol_type = protein
                       note = strain CB1190
                       organism = Pseudonocardia dioxanivorans
SEQUENCE: 4
MQLLPGVRSV VVPTDRLEVH LVEYGPEEGV PVVMLHGNLS TGRFFEHLFP GAPQGYRIIA     60
PDMRCFGDTE RLPLDATRGL ADWADDVAAL LRALRVERPV HLLGWSTAGA AIVDFASAHP   120
VTSLTFLDPV SPYGFGGVLA DGTPCFPDFA GSGGGIVNPE VVRRLAEGDD TTESPFSIRS   180
VMRGSYWLES HSEPREDLLV AEVLKTVTGD DNYPGDSVAS PNWPGSAPGT TGIINALSPK   240
YCNWTRVVDL DPKPPVLWTH GAEDTVVADA SMQDLGTLGE LGYVPGWPGA DVFPSQPMVS   300
QIREVLGRYA AAGGHVRTEI LPGAGHSPHI ELPELWSGVF WDFVGAAERG              350

SEQ ID NO: 5           moltype = DNA  length = 1113
FEATURE                Location/Qualifiers
misc_feature           1..1113
                       note = Ecoli opt
source                 1..1113
                       mol_type = other DNA
                       organism = synthetic construct
SEQUENCE: 5
atgaccctgt ttgatggcat cacttcgcgt attgttgaca ccgatcgtct gaccgtgaat     60
attctggagc gtgcggcaga cgatccgcaa acgccgcctg atcgcacggt tgtttttgtg   120
catggtaacg tcagcagcgc gctgttttgg caagaaatta tgcaagacct cccgagcgat   180
ctgcgtgcta tcgcggtgga tctgcgtggc ttcggtggca gcgagcacgc accggtcgac   240
gcgacccgtg gtgttcgcga tttcagcgat gacttgcacg caacgctgga agcactggat   300
atcccggtcg cacacctggt cggttggagc atgggtggcg gcgtggttat gcagtatgca   360
ttagaccatc cggttttgag cctgacgctg cagtccccgg tcagcccgta cggttttcggt  420
ggcacccgtc gtgacggcag ccgtctgact gatgacgatg ctggctgcgg tggcggcggc   480
gccaatccgg atttcattca gcgtctgatc gaccacgaca cgtccgacga cgcgcagacn   540
agcccgcgct ccgttttccg tgcgggttac gtagcgagcg attaccacac ggaccacgaa   600
gatgtgtggg tggagagcat gctgaccacc tctaccgcgg acggcaatta cccaggtgac   660
gccgtcccga cgacaactg gccaggtttt ccgcgcggtc gccacggtgt tctgaacacg    720
atggcgcctc aatacttcga tgtcagcggt atcgttgatc tggcggagaa accgccgatt    780
ttgtggatcc atgtaccgc ggatgcgatt gtgtccgacg cagcttttta tgacctgacc     840
tatctgggtc agctgggtat cgtgccgggt tggccgggtg aagatgtcgc tccgcccaa    900
gaaatggtta gccagacgcg cgacgtcctg gccgttacg ctgcgggtgg cggcaccgtt    960
accgaagttg ccgttgaggg tgcgggtcac agcgcacatt ggagcgtcc ggccgtgttc   1020
cgccacgcgc tgctggaaat tattggttat gtgggtgcgg ctgctgaccc ggcaccgccg   1080
actgaagcaa tcatcatccg ctctgccgac taa                               1113

SEQ ID NO: 6           moltype = AA  length = 370
FEATURE                Location/Qualifiers
source                 1..370
                       mol_type = protein
                       organism = Microbacterium chocolatum
SEQUENCE: 6
MTLFDGITSR IVDTDRLTVN ILERAADDPQ TPPDRTVVFV HGNVSSALFW QEIMQDLPSD     60
LRAIAVDLRG FGGSEHAPVD ATRGVRDFSD DLHATLEALD IPVAHLVGWS MGGGVVMQYA   120
LDHPVLSLTL QSPVSPYGFG GTRRDGSRLT DDDAGCGGGG ANPDFIQRLI DHDTSDDAQT   180
```

```
SPRSVFRAGY VASDYTTDHE DVWVESMLTT STADGNYPGD AVPSDNWPGF AAGRHGVLNT    240
MAPQYFDVSG IVDLAEKPPI LWIHGTADAI VSDASFYDLN YLGQLGIVPG WPGEDVAPAQ    300
EMVSQTRDVL GRYAAGGGTV TEVAVEGAGH SAHLERPAVF RHALLEIIGY VGAAADPAPP    360
TEAIIIRSAD                                                          370

SEQ ID NO: 7              moltype = DNA   length = 894
FEATURE                   Location/Qualifiers
misc_feature              1..894
                          note = Ecoli opt
source                    1..894
                          mol_type = other DNA
                          organism = synthetic construct
SEQUENCE: 7
atggaaaagc gcagcattac tctgaaaaac ggtgaagttt acaaatacgt ggaacagggt     60
cagggcgacc aagttctgct gctgatccat ggcaacttta gctccagcct gcacttcacc    120
ccgttgctgg agcgcctgcc gaagaacatt aaggttattg cgccggactt gcgtggttat    180
ggtgattcat cttactatcg tcgtatcagc tctctgaacg acttcgcgga agatgtccac    240
atgtttatgg aagccaaaga aattaaaagc taccacgtag ttggctggag cctgggtggc    300
ggcgtggcgc tggaactggc ggcacatcat ccagaggctg tggagtcctt ggtgctcatc    360
aacagcacca cgcacaaggg ttatccggtg ttcaagaaag gtgcggatgg taagccactg    420
gtcggtgaag tctatcaaag cgccgatgag atggcaaatg atccggtcca agtcctgccg    480
ctgctgaagg ctcaaaaaga taagaatttt gactttgtta gctatatctt cgatgttacc    540
atttacaccg tgaataagcc ttcggtggat gacaacaagc tgtggattaa cgaaagcctg    600
aaacagcgta atctgccgga tgcagactgg gcgctggcga atttgaacat gagcgaccag    660
cacaatttct acaatgccgg tatgaacaat atctccaagg ttaaggcacc ggtgctgcac    720
acgtggggcg acaaagatat taccgtgccg gagtatatga tcaaagacaa tgtgaaagcg    780
ctggaagaac aaaagcaaact ggtcgtctac gagaactgcg gccatagccc gctggttgat    840
gttccggacc agctgacgaa agacatcctg gactttatcg gttacaaggg ttaa          894

SEQ ID NO: 8              moltype = AA   length = 297
FEATURE                   Location/Qualifiers
REGION                    1..297
                          note = patented sequence
source                    1..297
                          mol_type = protein
                          organism = unidentified
SEQUENCE: 8
MEKRSITLKN GEVYKYVEQG QGDQVLLLIH GNFSSSLHFT PLLERLPKNI KVIAPDLRGY     60
GDSSYYRRIS SLNDFAEDVH MFMEAKEIKS YHVVGWSLGG GVALELAAHH PEAVESLVLI    120
NSTTHKGYPV FKKGADGKPL VGEVYQSADE MANDPVQVLP LLKAQKDKNF DFVSYIFDVT    180
IYTVNKPSVD DNKLWINESL KQRNLPDADW ALANLNMSDQ HNFYNAGMNN ISKVKAPVLH    240
TWGDKDITVP EYMIKDNVKA LEEQSKLVVY ENCGHSPLVD VPDQLTKDIL DFIGYKG       297

SEQ ID NO: 9              moltype = DNA   length = 1470
FEATURE                   Location/Qualifiers
source                    1..1470
                          mol_type = genomic DNA
                          organism = Bacillus subtilis
                          strain = NBRC3027
SEQUENCE: 9
atgactcatc aaatagtaac gactcaatac ggcaaagtaa aaggcacaac agaaaatggc     60
gtacataaat ggaaaggcat cccctatgcc agaccgcctg tcgggccatt gcgttttaaa    120
gcaccggaac ctccggaagc gtgggagaac gaactggacg caacagcgta cggccctatt    180
tgcccgcagc cgtctgattt gctgtcactt tcgtataatg agctgccccg ccagtctgag    240
aattgcttgt atgtcaatgt attttgcgcct gatactccaa gtcaaaacct gcctgtcatg    300
gtgtggattc acggcggcgc ttttttatct ggagcgggca gtgagccatt attcgatgag    360
tcaagacttg cggcgcaggg agaagtcatt gtcgttacac tgaattatcg actgggggccg    420
tttggatttt tacatttgtc ttcgtttgat gaggcgtatt ccgataacct tggtctttttg    480
gaccaagccg ccgcactgaa atgggtgcga gacaatatct cagcatttgg cggtgatccg    540
gataacgtaa cggtatttgg agaatccgct ggcggcatga gcattgccgc gctgctcgca    600
atgcctgcgg caaaaggcct gttccagaaa gcgatcatgg aaagcggcgc ttctagaaca    660
atgacaacag aaaaagcggc tagcactgca gcagcctttt tacaggtcct tgggattaac    720
gagagccaat ggacagact gcacactgta tctgcggaag atttgcttaa agcggccgat    780
aagcttcgga aagcagaaaa tgaaaatctc tttcagctgt tattccagcc cgcccttgat    840
ccgaaaacgc tgcctgctga accagaaaaa gcaatcgcag gaggtgctgc tgccgacatt    900
ccgctgttaa tcggaacaaa ccgcgatgaa ggatatttat ttttcacccc ggactcagac    960
gttcattctc aagaaacgtt taatgccgcg cttgagtatt tattgaacac gccgctggca   1020
aagaaagccg acgatctgta tccgcgttca ctagaaagcc aaattcatat gatgactgat   1080
ttgttatttt ggcgcccggc cgtcgcctat gcctccgctc agtctcaata cgcgcctgta   1140
tggatgtacc gatttgattg gcactctgat aagccgccat acaataaggc gtttcacgca   1200
ttagagcttc ctttttgtttt cggaaatctg gacgggttag aacgaatggc aaaagcagag   1260
gttacggatg aggtgaaacg gcttttctcat accatacaat cagcatggat cacgtttgcc   1320
aaaacaggaa acccaagcac cgaagatgta aaatggccgg cgtatcatga agaaacaaga   1380
cagaagctga ttttagattc agagattacg atcgaaaacg atcctgaatc tgaaaaaagg   1440
cagaagctat tcccttcaaa aggagaataa                                    1470

SEQ ID NO: 10             moltype = AA   length = 489
FEATURE                   Location/Qualifiers
source                    1..489
```

```
                        mol_type = protein
                        note = strain NBRC3027
                        organism = Bacillus subtilis
SEQUENCE: 10
MTHQIVTTQY GKVKGTTENG VHKWKGIPYA RPPVGPLRFK APEPPEAWEN ELDATAYGPI    60
CPQPSDLLSL SYNELPRQSE NCLYVNVFAP DTPSQNLPVM VWIHGGAFYL GAGSEPLFDG   120
SRLAAQGEVI VVTLNYRLGP FGFLHLSSFD EAYSDNLGLL DQAAALKWVR DNISAFGGDP   180
DNVTVFGESA GGMSIAALLA MPAAKGLFQK AIMESGASRT MTTEKAASTA AFLQVLGIN    240
ESQLDRLHTV SAEDLLKAAD KLRKAENENL FQLLFQPALD PKTLPAEPEK AIAGGAAADI   300
PLLIGTNRDE GYLFFTPDSD VHSQETFNAA LEYLLEQPLA KKAADLYPRS LESQIHMMTD   360
LLFWRPAVAY ASAQSQYAPV WMYRFDWHSD KPPYNKAPHA LELPFVFGNL DGLERMAKAE   420
VTDEVKRLSH TIQSAWITFA KTGNPSTEDV KWPAYHEETR QTLILDSEIT IENDPESEKR   480
QKLFPSKGE                                                          489

SEQ ID NO: 11           moltype = DNA  length = 1470
FEATURE                 Location/Qualifiers
source                  1..1470
                        mol_type = genomic DNA
                        organism = Bacillus subtilis
                        strain = ATCC23857
SEQUENCE: 11
atgactcatc aaatagtaac gactcaatac ggcaaagtaa aaggcacaac ggaaaacggc     60
gtacataagt ggaaaggcat ccctatgcc aagccgcctg tcggacaatg gcgttttaaa    120
gcacctgagc cgcctgaagt gtgggaagat gtgcttgatg ccacagcgta cggctctatt    180
tgcccgcagc cgtctgattt gctgtcactt tcgtatactg agctgccccg ccagtccgag   240
gattgcttgt atgtcaatgt atttgcgcct gacacccoga taaaaatct tcctgtcatg    300
gtgtggattc acggaggcgc ttttatcta ggagcgggca gtgagccatt tatgacgga    360
tcaaaacttg cggcacaggg agaagtcatt gtcgttacat tgaactatcg gctgggccg    420
tttggctttt tgcacttgtc ttcatttaat gaggcgtatt ctgataacct tgggcttta    480
gaccaagccg ccgcgctgaa atgggtgcga gagaatattt cagcgttgg cggtgatccc    540
gataacgtaa cagtatttgg agaatccgcc ggcgggtga gcattgccgc gctgcttgct   600
atgcctgcgg caaaaggcct gttccagaaa gcaatcatgg aaagcggcgc ttctcgaacg   660
atgacgaaaa acaagcggc gagcacctcg gcagccttt tacaggtcct tgggattaac   720
gagggccaac tggataaatt gcatacggtt tctgcggaaa atttgctaaa agcggctgat   780
cagcttcgga ttgcagaaaa agaaaatatc tttcagctgt tcttccagcc cgcccttgat   840
ccgaaaacgc tgcctgaaga accagaaaaa gcgatcgcag aaggggctgc ttccggtatt   900
ccgctattaa ttggaacaac ccgtgatgaa ggatatttat ttttcacccc ggattcagac   960
gttcattctc aggaaacgct tgatgcagcg ctcgagtatt tactagggaa gccgctggca  1020
gagaaagttg ccgatttgta tccgcgttct ctggaaagcc aaattcatat gatgactgat  1080
ttattattt ggcgccctgc cgtcgcctat gcatccgcac agtctcatta cgccccctgtc  1140
tggatgtaca ggttcgattg cacccgaag aagccgccgt acaataaagc gtttcacgca  1200
ttagagcttc cttttgtctt tggaaatctg acggattgg aacgaatggc aaaagcggag  1260
attacggatg aggtgaaaca gctttctcac acgatacaat cagcgtggat cacgttcgcc  1320
aaaacaggaa acccaagcac cgaagctgtg aattggcctg cgtatcatga gaaaacgaga  1380
gagacgctga ttttagactc agagattacg atcgaaaacg atcccgaatc tgaaaaaagg  1440
cagaagctat tcccttcaaa aggagaataa                                    1470

SEQ ID NO: 12           moltype = AA  length = 489
FEATURE                 Location/Qualifiers
source                  1..489
                        mol_type = protein
                        note = strain ATCC23857
                        organism = Bacillus subtilis
SEQUENCE: 12
MTHQIVTTQY GKVKGTTENG VHKWKGIPYA KPPVGQWRFK APEPPEVWED VLDATAYGSI    60
CPQPSDLLSL SYTELPRQSE DCLYVNVFAP DTPSKNLPVM VWIHGGAFYL GAGSEPLYDG   120
SKLAAQGEVI VVTLNYRLGP FGFLHLSSFN EAYSDNLGLL DQAAALKWVR ENISAFGGDP   180
DNVTVFGESA GGMSIAALLA MPAAKGLFQK AIMESGASRT MTKEQAASTS AAFLQVLGIN   240
EGQLDKLHTV SAEDLLKAAD QLRIAEKENI FQLFFQPALD PKTLPEEPEK AIAEGAASGI   300
PLLIGTTRDE GYLFFTPDSD VHSQETLDAA LEYLLGKPLA EKVADLYPRS LESQIHMMTD   360
LLFWRPAVAY ASAQSHYAPV WMYRFDWHPK KPPYNKAPHA LELPFVFGNL DGLERMAKAE   420
ITDEVKQLSH TIQSAWITFA KTGNPSTEAV NWPAYHEETR ETLILDSEIT IENDPESEKR   480
QKLFPSKGE                                                          489

SEQ ID NO: 13           moltype = DNA  length = 33
FEATURE                 Location/Qualifiers
misc_feature            1..33
                        note = primer
source                  1..33
                        mol_type = other DNA
                        organism = synthetic construct
SEQUENCE: 13
gcgaattcat gactcatcaa atagtaacga ctc                                 33

SEQ ID NO: 14           moltype = DNA  length = 33
FEATURE                 Location/Qualifiers
misc_feature            1..33
                        note = primer
source                  1..33
```

```
                            mol_type = other DNA
                            organism = synthetic construct
SEQUENCE: 14
gctctagatt attctccttt tgaagggaat agc                                33

SEQ ID NO: 15               moltype = DNA   length = 32
FEATURE                     Location/Qualifiers
misc_feature                1..32
                            note = primer
source                      1..32
                            mol_type = other DNA
                            organism = synthetic construct
SEQUENCE: 15
tcccccgggg tcaaggcgca ctcccgttct gg                                 32

SEQ ID NO: 16               moltype = DNA   length = 35
FEATURE                     Location/Qualifiers
misc_feature                1..35
                            note = primer
source                      1..35
                            mol_type = other DNA
                            organism = synthetic construct
SEQUENCE: 16
tcccccgggg tggggtgcct aatgagtgag ctaac                              35

SEQ ID NO: 17               moltype = DNA   length = 40
FEATURE                     Location/Qualifiers
misc_feature                1..40
                            note = primer
variation                   19..20
                            note = n is a, c, g, or t
source                      1..40
                            mol_type = other DNA
                            organism = synthetic construct
SEQUENCE: 17
ccgtctgatt tgctgtcann ktcgtataat gagctgcccc                         40

SEQ ID NO: 18               moltype = DNA   length = 40
FEATURE                     Location/Qualifiers
misc_feature                1..40
                            note = primer
variation                   21..22
                            note = n is a, c, g, or t
source                      1..40
                            mol_type = other DNA
                            organism = synthetic construct
SEQUENCE: 18
ggggcagctc attatacgam nntgacagca aatcagacgg                         40

SEQ ID NO: 19               moltype = DNA   length = 32
FEATURE                     Location/Qualifiers
misc_feature                1..32
                            note = primer
variation                   17..18
                            note = n is a, c, g, or t
source                      1..32
                            mol_type = other DNA
                            organism = synthetic construct
SEQUENCE: 19
ccgcgatgaa ggatatnnkt ttttcacccc gg                                 32

SEQ ID NO: 20               moltype = DNA   length = 32
FEATURE                     Location/Qualifiers
misc_feature                1..32
                            note = primer
variation                   15..16
                            note = n is a, c, g, or t
source                      1..32
                            mol_type = other DNA
                            organism = synthetic construct
SEQUENCE: 20
ccggggtgaa aaamnnatat ccttcatcgc gg                                 32

SEQ ID NO: 21               moltype = DNA   length = 53
FEATURE                     Location/Qualifiers
misc_feature                1..53
                            note = primer
variation                   26..27
                            note = n is a, c, g, or t
```

```
variation          35..36
                   note = n is a, c, g, or t
source             1..53
                   mol_type = other DNA
                   organism = synthetic construct
SEQUENCE: 21
gcttcggaaa gcagaaaatg aaaatnnktt tcagnnktta ttccagcccg ccc        53

SEQ ID NO: 22      moltype = DNA  length = 53
FEATURE            Location/Qualifiers
misc_feature       1..53
                   note = primer
variation          18..19
                   note = n is a, c, g, or t
variation          27..28
                   note = n is a, c, g, or t
source             1..53
                   mol_type = other DNA
                   organism = synthetic construct
SEQUENCE: 22
gggcgggctg gaataamnnc tgaaamnnat tttcattttc tgctttccga agc        53

SEQ ID NO: 23      moltype = DNA  length = 1470
FEATURE            Location/Qualifiers
source             1..1470
                   mol_type = other DNA
                   organism = Bacillus subtilis
                   strain = NBRC3027
SEQUENCE: 23
atgactcatc aaatagtaac gactcaatac ggcaaagtaa aaggcacaac agaaaatggc   60
gtacataaat ggaaaggcat cccctatgcc agaccgcctg tcgggccatt gcgttttaaa  120
gcaccggagc ctccggaagc gtgggagaac gaactggacg caacagcgta cggccctatt  180
tgcccgcagc cgtctgattt gctgtcagat tcgtataatg agctgccccg ccagtctgag  240
aattgcttgt atgtcaatgt atttgcgcct gatactccaa gtcaaaacct gcctgtcatg  300
gtgtggattc acggcggcgc ttttatcttc ggagcgggca gtgagccatt attcgatggg  360
tcaagacttg cggcgcaggg agaagtcatt gtcgttacac tgaattatcg actggggccg  420
tttgattttt tacatttgtc ttcgtttgat gaggcgtatt ccgataacct tggtcttttg  480
gaccaagccg ccgcactgaa atgggtgcga gacaatatct cagcatttgg cggtgatccg  540
gataacgtaa cggtatttgg agaatccgct ggcggcatga gcattgccgc gctgctcgca  600
atgcctgcgg caaaaggcct gttccagaaa gcgatcatgg aaagcggcgc ttctagaaca  660
atgacaacag aaaaagcggc tagcactgca gcagcctttt tacaggtcct tgggattaac  720
gagagccaat tggacagact gcacactgta tctgcggaag atttgcttaa agcggccgat  780
aagcttcgga aagcagaaaa tgaaaatcag tttcagcggt tattccagcc cgcccttgca  840
ccgaaaacgc tgcctgctga accagaaaaa gcaatcgcag gaggtgctgc tgccgacatt  900
ccgctgttaa tcggaacaaa ccgcgatgaa ggatatatgt ttttcacccc ggactcagac  960
gttcattctc aagaaacgtt taatgccgcg cttgagtatt tattggaaca gccgctggca 1020
aagaaagccg ccgatctgta tccgcgttca ctagaaagcc aaattcatat gatgactgat 1080
ttgttatttt ggcgcccggc cgtcgcctat gcctccgctc agtctcaata cgcgcctgta 1140
tggatgtacc gatttgattg gcactctgat aagccgccat acaataaggc gtttcacgca 1200
ttagagcttc cttttgtttt cggaaatctg gacgggttag aacgaatggc aaaagcagag 1260
gttacggatg aggtgaaacg gcttctcat accatacaat cagcatggat cacgtttgcc 1320
aaaacaggaa acccaagcac cgaagatgta aaatggccgg cgtatcatga agaaacaaga 1380
cagacgctga ttttagattc agagattacg atcgaaaacg atcctgaatc tgaaaaaagg 1440
cagaagctat tcccttcaaa aggagaataa                                  1470

SEQ ID NO: 24      moltype = AA  length = 489
FEATURE            Location/Qualifiers
source             1..489
                   mol_type = protein
                   note = strain NBRC3027
                   organism = Bacillus subtilis
SEQUENCE: 24
MTHQIVTTQY GKVKGTTENG VHKWKGIPYA RPPVGPLRFK APEPPEAWEN ELDATAYGPI   60
CPQPSDLLSD SYNELPRQSE NCLYVNVFAP DTPSQNLPVM VWIHGGAFYL GAGSEPLFDG  120
SRLAAQGEVI VVTLNYRLGP FGFLHLSSFD EAYSDNLGLL DQAAALKWVR DNISAFGGDP  180
DNVTVFGESA GGMSIAALLA MPAAKGLFQK AIMESGASRT MTTEKAASTA AAFLQVLGIN  240
ESQLDRLHTV SAEDLLKAAD KLRKAENENQ FQRLFQPALD PKTLPAEPEK AIAGGAAADI  300
PLLIGTNRDE GYMFFTPDSD VHSQETFNAA LEYLLEQPLA KKAADLYPRS LESQIHMMTD  360
LLFWRPAVAY ASAQSQYAPV WMYRFDWHSD KPPYNKAFHA LELPFVFGNL DGLERMAKAE  420
VTDEVKRLSH TIQSAWITFA KTGNPSTEDV KWPAYHEETR QTLILDSEIT IENDPESEKR  480
QKLFPSKGE                                                         489
```

What is claimed is:

1. A method for producing (1S,2S)-1-alkoxycarbonyl-2-vinylcyclopropane carboxylic acid, comprising bringing a hydrolase, a microorganism or cell having an ability to produce the hydrolase, a and/or a culture solution containing the hydrolase into contact with dialkyl 2-vinylcyclopropane-1,1-dicarboxylic acid represented by formula (I) to produce (1S,2S)-1-alkoxycarbonyl-2-vinylcyclopropane carboxylic acid represented by formula (II), wherein the hydrolase comprises a polypeptide of the following (a), (b), or (c):

(a) a polypeptide consisting of an amino acid sequence resulting from the deletion, insertion, substitution, and/or addition of 1 to 50 amino acids in the amino acid sequence shown in SEQ ID NO: 4 or 6, and an activity to catalyze the reaction shown in the formula (1):

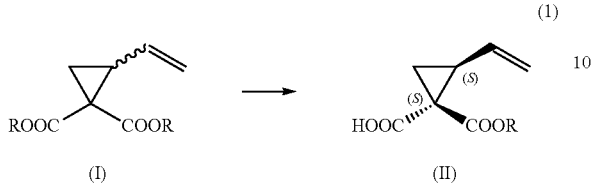

wherein R is an alkyl group having 1 to 6 carbon atoms, and a ratio of Syn isomer to Anti isomer in formula (II) is equal to or less than 0.2%;
  (b) a polypeptide consisting of an amino acid sequence with not less than 95% sequence identity with the amino acid sequence shown in SEQ ID NO: 4 or 6, and an activity to catalyze the reaction shown in formula (1);
  (c) a polypeptide consisting of an amino acid sequence with not less than 90% sequence identity with the amino acid sequence shown in SEQ ID NO: 4 or 6, wherein the amino acid sequence comprises:
    (i) 5 consecutive residues DATRG corresponding to residues 75-79 of SEQ ID NO: 4 and residues 80-84 of SEQ ID NO: 6;
    ii 4 consecutive residues PYGF corresponding to residues 132-135 of SEQ ID NO: 4 and residues 136-139 of SEQ ID NO: 6;
    iii 4 consecutive residues NWPG corresponding to residues 222-225 of SEQ ID NO: 4 and residues 226-229 of SEQ ID NO: 6; and/or
    (iv) 5 consecutive residues PGWPG corresponding to residues 285-289 of SEQ ID NO: 4 and residues 289-293 of SEQ ID NO: 6.

2. The production method according to claim 1, wherein R in the formula (1) is an ethyl group.

3. The production method according to claim 1, wherein the microorganism or cell is a microorganism or cell transformed with a nucleic acid encoding the hydrolase comprising the polypeptide of following (a), (b), or (c).

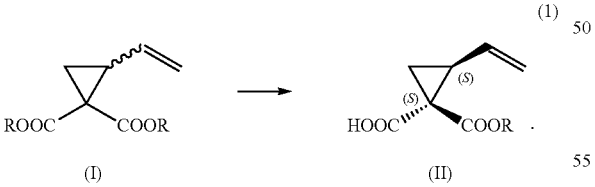

4. The production method according to claim 1, wherein the microorganism or cell is a microorganism or cell transformed with a nucleic acid comprising a base sequence of the following (d), (e), (f), or (g):
  (d) the base sequence shown in SEQ ID NO: 3 or 5;
  (e) a nucleic acid consisting of a base sequence resulting from the substitution, deletion, and/or addition of 1 to 150 bases in the base sequence shown in SEQ ID NO: 3 or 5, and encoding a polypeptide having an activity to catalyze the reaction shown in formula (1);

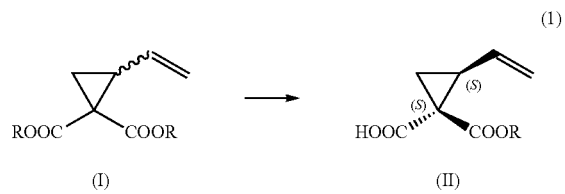

wherein R is an alkyl group having 1 to 6 carbon atoms in formula (1), and wherein the ratio of Syn isomer to Anti isomer in formula (II) is equal to or less than 0.2%;
  (f) a nucleic acid consisting of a base sequence having not less than-60% of 90% sequence identity with the base sequence shown in SEQ ID NO: 3 or 5, and encoding a polypeptide having an activity to catalyze the reaction shown in formula (1);
  (g) a nucleic acid having a base sequence that hybridizes with a complementary strand of the base sequence shown in SEQ ID NO: 3 or 5 under the condition of washing once at 60° C., 1×SSC, and 0.1% SDS, and encoding a polypeptide having an activity to catalyze the reaction shown informula (1).

5. A method for producing (1S,2S)-1-alkoxycarbonyl-2-vinylcyclopropane carboxylic acid, comprising bringing a treated product of a microorganism or cell having the ability to produce a hydrolase into contact with dialkyl 2-vinylcyclopropane-1,1-dicarboxylic acid represented by formula (I) to produce (1S,2S)-1-alkoxycarbonyl-2-vinylcyclopropane carboxylic acid represented by formula (II),
  wherein the hydrolase comprises a polypeptide of the following (a), (b), or (c):
  (a) a polypeptide consisting of an amino acid sequence resulting from the deletion, insertion, substitution, and/or addition of 1 to 50 amino acids in the amino acid sequence shown in SEQ ID NO: 4 or 6, and an activity to catalyze the reaction shown in formula (1):

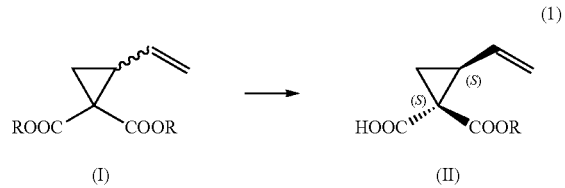

wherein R is an alkyl group having 1 to 6 carbon atoms, and a ratio of Syn isomer to Anti isomer in formula (II) is equal to or less than 0.2%;
  (b) a polypeptide consisting of an amino acid sequence with not less than 95% sequence identity with the amino acid sequence shown in SEQ ID NO: 4 or 6, and an activity to catalyze the reaction shown in formula (1);
  (c) a polypeptide consisting of an amino acid sequence with not less than 90% sequence identity with the amino acid sequence shown in SEQ ID NO: 4 or 6, wherein the amino acid sequence comprises:
    (i) 5 consecutive residues DATRG corresponding to residues 75-79 of SEQ ID NO: 4 and residues 80-84 of SEQ ID NO: 6;

(ii) 4 consecutive residues PYGF corresponding to residues 132-135 of SEQ ID NO: 4 and residues 136-139 of SEQ ID NO: 6;
(iii) 4 consecutive residues NWPG corresponding to residues 222-225 of SEQ ID NO: 4 and residues 226-229 of SEQ ID NO: 6; and/or
(iv) 5 consecutive residues PGWPG corresponding to residues 285-289 of SEQ ID NO: 4 and residues 289-293 of SEQ ID NO: 6.

6. The production method according to claim 5, wherein R in the formula (1) is an ethyl group.

7. The production method according to claim 5, wherein the microorganism or cell is a microorganism or cell transformed with a nucleic acid comprising a base sequence of the following (d), (e), (f), or (g):

(d) the base sequence shown in SEQ ID NO: 3 or 5;
(e) a nucleic acid consisting of a base sequence resulting from the substitution, deletion, and/or addition of 1 to 150 bases in the base sequence shown in SEQ ID NO: 3 or 5, and encoding a polypeptide having an activity to catalyze the reaction shown in formula (1):

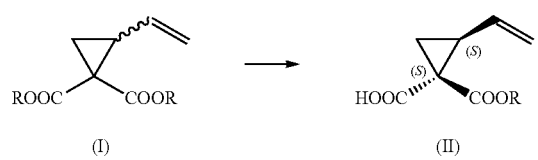

wherein R is an alkyl group having 1 to 6 carbon atoms in formula (1), and the ratio of Syn isomer to Anti isomer in formula (II) is equal to or less than 0.2%;

(f) a nucleic acid consisting of a base sequence having not less than 90% of sequence identity with the base sequence shown in SEQ ID NO: 3 or 5, and encoding a polypeptide having an activity to catalyze the reaction shown in formula (1);
(g) a nucleic acid having a base sequence that hybridizes with a complementary strand of the base sequence shown in SEQ ID NO: 3 or 5 under the condition of washing once at 60° C., 1×SSC, and 0.1% SDS, and encoding a polypeptide having an activity to catalyze the reaction shown in formula (1).

* * * * *

UNITED STATES PATENT AND TRADEMARK OFFICE
CERTIFICATE OF CORRECTION

PATENT NO. : 12,258,593 B2
APPLICATION NO. : 18/091687
DATED : March 25, 2025
INVENTOR(S) : Toyokazu Yoshida et al.

It is certified that error appears in the above-identified patent and that said Letters Patent is hereby corrected as shown below:

In the Claims

Column 33, Line 66 (Claim 1): please change "a and/or" to -- and/or --
Column 35, Line 32 (Claim 1): please change "ii" to -- (ii) --
Column 35, Line 35 (Claim 1): please change "iii" to -- (iii) --
Column 35, Line 47 (Claim 3): please change "of following (a)" to -- of (a) --
Column 36, Line 15 (Claim 4): please change "than-60% of 90%" to -- than 90% --

Signed and Sealed this
First Day of July, 2025

Coke Morgan Stewart
*Acting Director of the United States Patent and Trademark Office*